(12) United States Patent
Stamp

(10) Patent No.: US 7,744,561 B2
(45) Date of Patent: Jun. 29, 2010

(54) NEEDLELESS INJECTION DEVICE

(75) Inventor: Kevin Stamp, Sheffield (GB)

(73) Assignee: The Medical House Plc, Sheffield (GB)

( * ) Notice: Subject to any disclaimer, the term of this patent is extended or adjusted under 35 U.S.C. 154(b) by 1199 days.

(21) Appl. No.: 10/532,253

(22) PCT Filed: Oct. 20, 2003

(86) PCT No.: PCT/GB03/04532

§ 371 (c)(1),
(2), (4) Date: Sep. 15, 2005

(87) PCT Pub. No.: WO2004/037328

PCT Pub. Date: May 6, 2004

(65) Prior Publication Data

US 2006/0129089 A1    Jun. 15, 2006

(30) Foreign Application Priority Data

Oct. 22, 2002    (GB) ................. 0224505.8

(51) Int. Cl.
A61M 5/30 (2006.01)
(52) U.S. Cl. .......... 604/68; 604/131; 604/134; 604/135; 604/137; 604/240; 604/500; 604/187
(58) Field of Classification Search .......... 604/68, 604/18, 187, 15, 16, 72, 63, 6.11, 6.12, 36, 604/70, 118, 124, 137, 134, 240, 500, 131, 604/533, 538, 432; 279/2.23, 2.15, 2.1

See application file for complete search history.

(56) References Cited

U.S. PATENT DOCUMENTS 2,762,369 A    9/1956    Venditty (Continued)

FOREIGN PATENT DOCUMENTS

EP    1 291 028 A2    3/2003

(Continued)

Primary Examiner—Nicholas D Lucchesi
Assistant Examiner—Jenner Yeh
(74) Attorney, Agent, or Firm—Christensen O'Connor Johnson Kindness PLLC

(57) ABSTRACT

A needleless injection device comprising a cylinder for medicine having an injection nozzle at a forward end thereof and an opening at its rearward end; a piston sliding in the cylinder through said open end, in use, to drive the medicine through the nozzle; a ram to drive the piston into the cylinder and having a longitudinal axis; and a mechanical energy accumulator to drive the ram when discharged and disposed between the ram and a discharge assembly, a rear end of the ram extending into said discharge assembly; wherein the discharge assembly comprises a retention member fixed in the assembly, said retention member having a plurality of retention elements spaced around and adapted to locate on the ram when in a charged position of the ram, and a release ring surrounding said retention elements to prevent radial outward displacement thereof and discharge of the ram; and wherein axial displacement of said release ring releases said retention elements and causes discharge of the ram by said accumulator; characterized in that said retention elements are integral with said retention member and each has an enlarged head which can move into and out of engagement with a groove or recess on the ram by deformation of the material of said retention member.

22 Claims, 28 Drawing Sheets

U.S. PATENT DOCUMENTS

| | | | |
|---|---|---|---|
| 2,762,370 A | 9/1956 | Venditty | |
| 4,089,334 A | 5/1978 | Schwebel | |
| 5,062,830 A | 11/1991 | Dunlap | |
| 5,383,858 A * | 1/1995 | Reilly et al. | 604/152 |
| 5,782,802 A | 7/1998 | Landau | |
| 5,865,795 A * | 2/1999 | Schiff et al. | 604/70 |
| 5,875,976 A | 3/1999 | Stoeckmann et al. | |
| 5,891,086 A | 4/1999 | Weston | |
| 6,039,303 A * | 3/2000 | Danielson et al. | 251/149.6 |
| 6,099,503 A | 8/2000 | Stradella | |
| 6,383,168 B1 | 5/2002 | Bonicatto et al. | |
| 6,669,664 B2 * | 12/2003 | Slate et al. | 604/68 |
| 6,752,781 B2 * | 6/2004 | Landau et al. | 604/70 |
| 7,273,477 B2 * | 9/2007 | Spohn et al. | 604/500 |
| 2001/0039394 A1 | 11/2001 | Weston | |
| 2002/0058908 A1 * | 5/2002 | Zierenberg et al. | 604/72 |
| 2003/0040697 A1 * | 2/2003 | Pass et al. | 604/21 |

FOREIGN PATENT DOCUMENTS

| | | |
|---|---|---|
| FR | 2 718 356 A1 | 10/1995 |
| GB | 993309 A | 5/1965 |
| WO | WO 02/47746 A1 | 6/2002 |
| WO | WO 03/070296 A2 | 8/2003 |

* cited by examiner

NEEDLELESS INJECTION DEVICE

This invention relates to the field of needleless injection devices of the type used, for example, for subcutaneous injection of insulin or growth hormone.

Needleless injection devices (or "needleless injectors") are well known and are designed to deliver a predetermined dose of a drug, for example insulin, by means of a spring-loaded or gas-powered syringe. One typical such needleless injector is described in U.S. Pat. No. 5,782,802 [Vitajet Corp].

The device described in U.S. Pat. No. 5,782,802 is designed to be easily refilled and reused by a single user with the correct dose of a medicament required at each injection. The device comprises basically of:

a) an injection head comprising a transparent thermoplastic generally cylindrical nozzle and a thermoplastic piston tip, both supplied to the user in a sterile pack;
b) a spring-powered unit with means to quickly attach and detach the injection head from this spring-powered unit; and
c) a pre-filled special vial (containing the medicament) which connects to the injection head, or alternatively an adaptor which is attached to a commercially-available vial of medicament.

A dose of medicament is loaded into the device of U.S. Pat. No. 5,782,802 by turning a dosage drum in an anti-clockwise direction so as to draw a quantity of medicament into the nozzle. When activated by the user, the injector delivers the medicament by expelling it rapidly through a small aperture in the nozzle so that the medicament passes through the patient's skin.

The delivery of a medicament using a needleless injector is typically much less traumatic than using a conventional syringe with a needle. This is because the nozzle aperture is usually of smaller diameter than a hypodermic needle and secondly because the medicament is delivered more rapidly using a needleless injector than by using a needle.

Examples of autoinjectors having a needle for puncturing the skin are described in U.S. Pat. No. 6,099,503 (Stradella) and WO 02/47746 (SEL Medical AB).

Conventional needleless injectors of the type described above have a relatively noisy operation owing to the use of ball bearings in the discharge mechanism. The discharge mechanism of U.S. Pat. No. 5,782,802 is described therein with reference to FIG. 1 (see column 5, line 39-column 6 line 22). In particular, ball bearings 48 are trapped between the ram' rear neck 36 and the inner front end of the bushing 44. In this position, the ball bearings 48 lock the ram 34 to the discharge mechanism 32. In order to discharge the device, the bushing 44 has to move forward allowing ball bearings 48 to move outward, away from the ram's neck 36, which consequently allows the ram's rear shoulder 38 to pass through, pushed vigorously by the fully compressed main spring 22.

The movement of the ball bearings 48 is only limited by the confines of the relevant parts of the device in which they are located. It is possible that the ball bearings will "rattle" within those confines, especially given the great force stored in the fully compressed main spring which is suddenly released upon discharge of the device, causing the ball bearings to be pushed vigorously. This "rattle" means that the device has a relatively noisy discharge operation.

The "rattle" (i.e. reverberation) of the ball bearings also has an adverse effect on the smoothness with which the medicament is delivered. It is important to minimise lateral movement of the injector during operation else trauma to the skin may result and therefore there is a desire to improve the smoothness of the injector's operation.

It is therefore an object of the present invention to provide a needleless injector which seeks to minimise the trauma to a patient's skin at the injection site, whilst also providing a quiet and smooth delivery of medicament to the patient.

According to a first aspect of the invention there is provided a needleless injection device comprising
- a cylinder for medicament having an injection nozzle at a forward end thereof and an opening at its rearward end;
- a piston sliding in the cylinder through said open end, in use, to drive the medicament through the nozzle;
- a ram to drive the piston into the cylinder and having a longitudinal axis; and
- an energy accumulator to drive the ram when discharged and disposed between the ram and a discharge assembly, a rear end of the ram extending into said discharge assembly; wherein
- the discharge assembly comprises a retention member fixed in the assembly, said retention member having a plurality of retention elements spaced around and adapted to locate on the ram when in a charged position of the ram, and a release ring surrounding said retention elements to prevent radial outward displacement thereof and discharge of the ram; and wherein
- axial displacement of said release ring releases said retention elements and causes discharge of the ram by said accumulator;

characterised in that said retention elements are integral with said retention member and each has an enlarged head which can move into and out of engagement with a groove or recess in the ram by deformation of the material of said retention member.

Since the ram is discharged by means of deformation of the material of the retention elements, the "rattle" or reverberation of the prior art device, caused by ball bearings or the like, is eliminated. The discharge of the device is much smoother, more controlled and quieter than that of conventional devices.

Preferably, said retention member comprises a collet having radially-spreadable fingers, which collet in use moves between said first position in which said fingers engage with said ram and said second position in which said fingers spread radially out of engagement with said ram.

Preferably, said collet fingers are biassed radially-inwardly.

Preferably, said release ring comprises a collet lock sleeve which limits outward radial movement of said collet fingers. Ideally, axial movement of said collet lock sleeve is limited by abutment thereof against said collet fingers.

Preferably, said collet lock sleeve and said collet fingers are respectively provided with cooperating tapered surfaces.

In a preferred embodiment said energy accumulator is a compression spring.

In a preferred form, the device further comprises a nozzle lock assembly which enables a nozzle to be releasably attached to said device upon insertion of a nozzle into an end thereof, the nozzle lock assembly including
- on one of said nozzle or said end of the injection device, a twist cap containing a moveable spacer which has a non-circular aperture therethrough; and
- on the other of said nozzle or said end of the injection device a protrusion having a correspondingly shaped non-circular outer surface which, if aligned therewith, can pass through said non-circular aperture,
- wherein, upon twisting of said twist cap, the moveable spacer twists with respect to said protrusion so that the non-circular aperture of the spacer can be selectively brought into and out of alignment with the non-circular outer surface of said protrusion, so that said protrusion is respectively either free to move in or out of said aperture or is trapped therein by said moveable spacer.

Preferably, said twist cap is located on said end of the injection device and said protrusion is located on said nozzle.

Preferably, the nozzle lock assembly further comprises a second protrusion having the same non-circular outer surface and being axially spaced from the first protrusion.

Preferably, said non-circular aperture and said non-circular outer surface are substantially triangular.

Preferably, the nozzle lock assembly further comprises a mark on said twist cap which indicates the relative alignment of the non-circular apertures.

In a preferred embodiment, the axial displacement is provided by means of a resistance-sensitive trigger comprising an axially-moveable shroud forming at least part of the outer surface of said device, the trigger being activated by application of forward axial force to the shroud which is resisted by the skin of the patient at an injection site.

Preferably, said resistance-sensitive trigger further comprises a safety-lock, moveable between a locked position, in which the device cannot be discharged and an unlocked position in which the device can be discharged. Further, preferably, said safety lock comprises at least one axially-extending tab which serves as an endstop which, in said locked position, prevents axial movement of said shroud. Advantageously, said tab is driveable between said locked and said unlocked positions by a rotatable drive plate actuated by a switch.

In a preferred form, in said unlocked position, said tab moves axially rearward to engage in a recess in an endcap of the injection device and, optionally, said tab is rearwardly biassed by means of a spring.

In a preferred embodiment, said energy accumulator is a spring confined within a variable-volume chamber, the injection device further comprising an integral firing force adjustment mechanism which, in use, varies the volume of said chamber, effected by rotation of said ram, optionally wherein the rotation of the ram is effected by the turning of a key inserted through one end of said device.

According to a second aspect of the invention there is provided a discharge assembly, suitable for use in a needleless injection device as described in any of the preceding paragraphs, comprising a retention member fixed in the assembly, said retention member having a plurality of retention elements spaced around and adapted to locate on a ram when in a charged position of the ram, and a release ring surrounding said retention elements to prevent radial outward displacement thereof and discharge of the ram; and wherein axial displacement of said retention ring releases said retention elements and causes discharge of the ram by an energy accumulator;

characterised in that said retention elements are integral with said retention member and each has an enlarged head which can move into and out of engagement with a groove or recess on said ram by deformation of the material of said retention member.

Preferred embodiments of the present invention will now be more particularly described, by way of example only, with reference to the accompanying drawings wherein.

Throughout the following description, reference to a "forward" direction means the direction which is towards the patient when the injector is in use. The "forward" end of the injector is the end nearest the patient's skin when the injector is in use. Similarly, reference to a "rearward" direction means the direction which is away from the patient and the "rearward" end of the injector is the end furthest from the patient's skin when the injector is in use.

Figure 1:
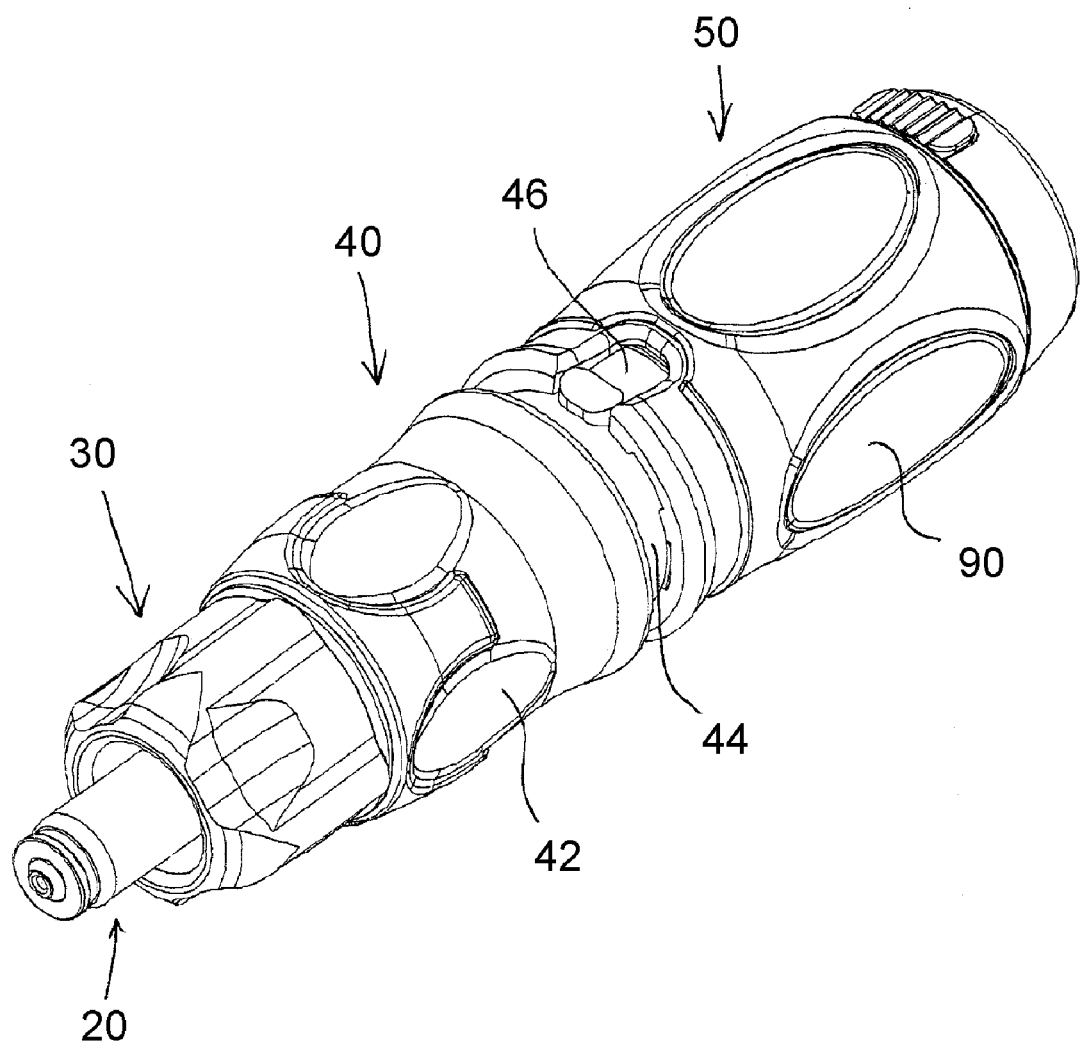
FIG. 1 is a perspective view of a needleless injection device embodying the first aspect of the invention.
Figure 2:
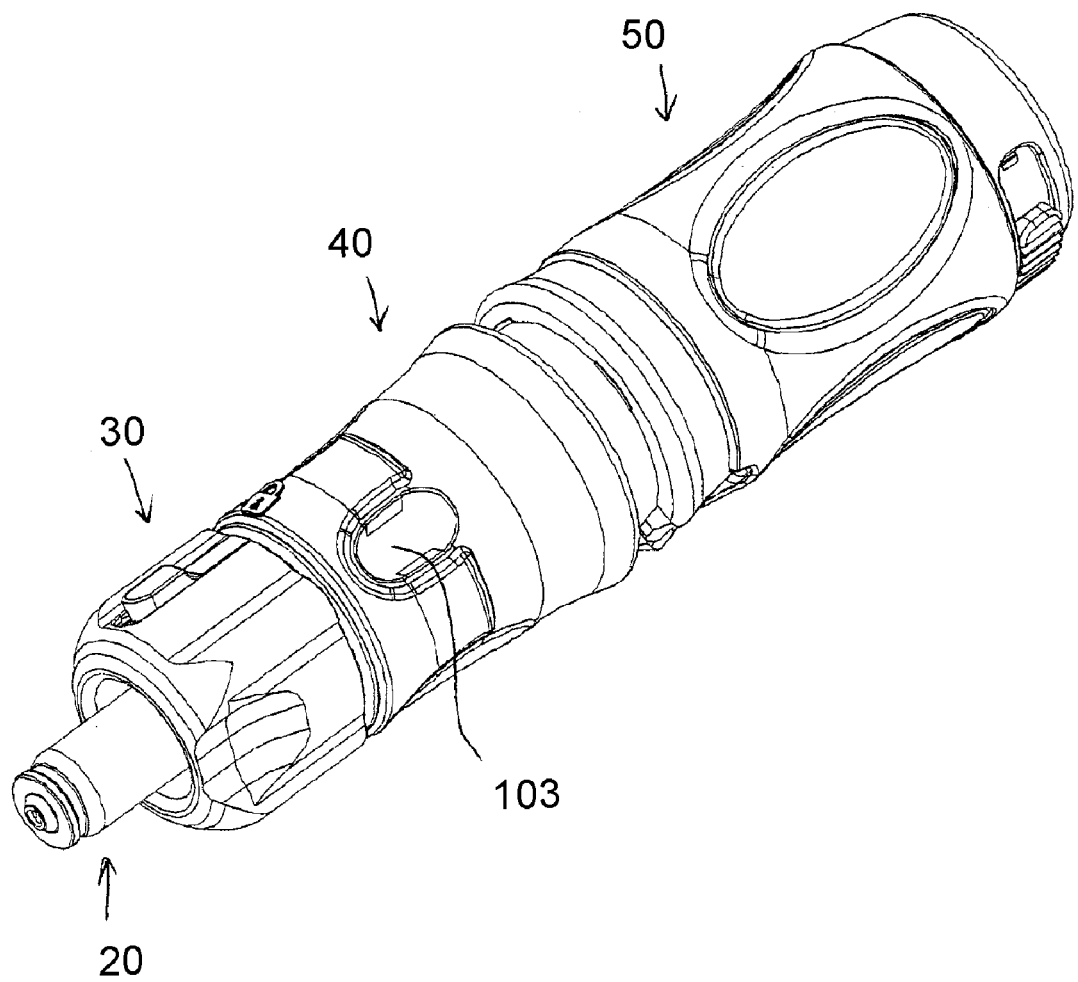
FIG. 2 is a further perspective view of the FIG. 1 injector.
Figure 12:
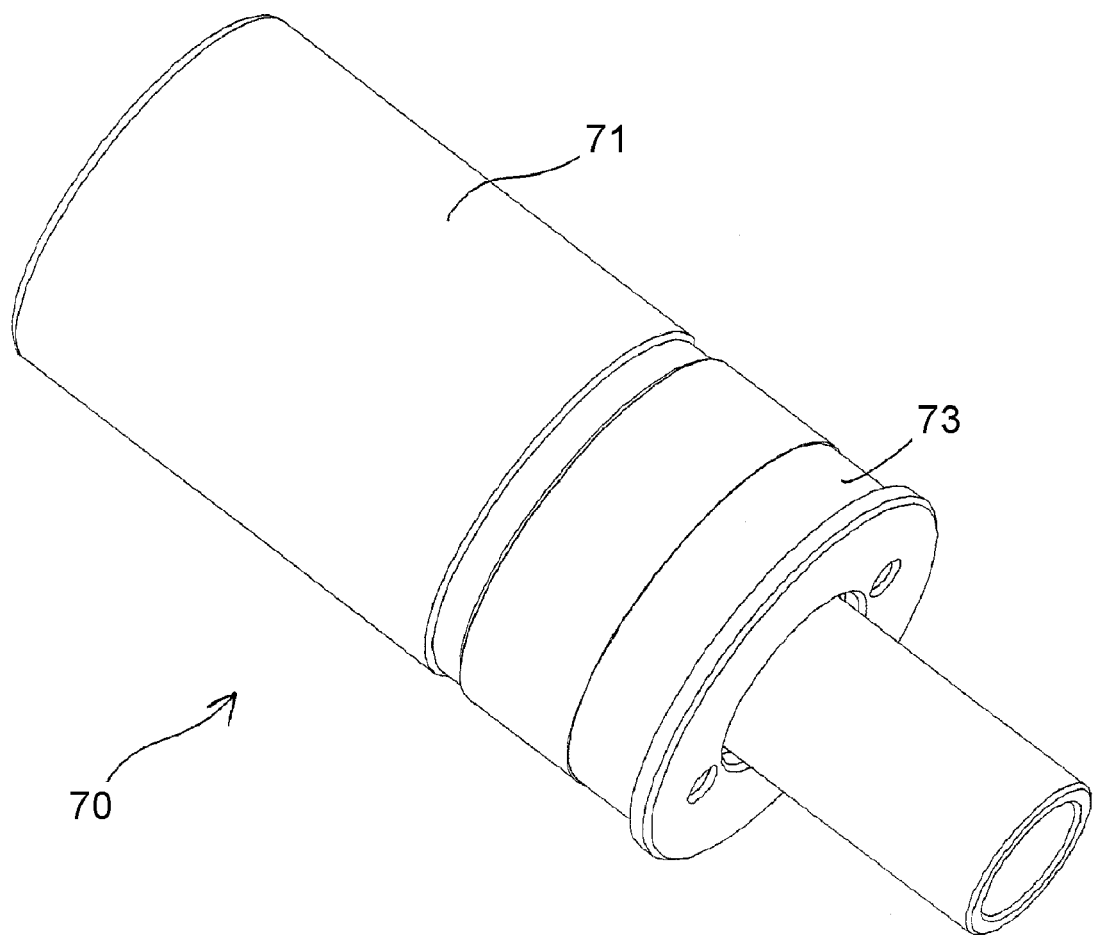
FIG. 12 is a perspective view of the discharge assembly.
Figure 13:
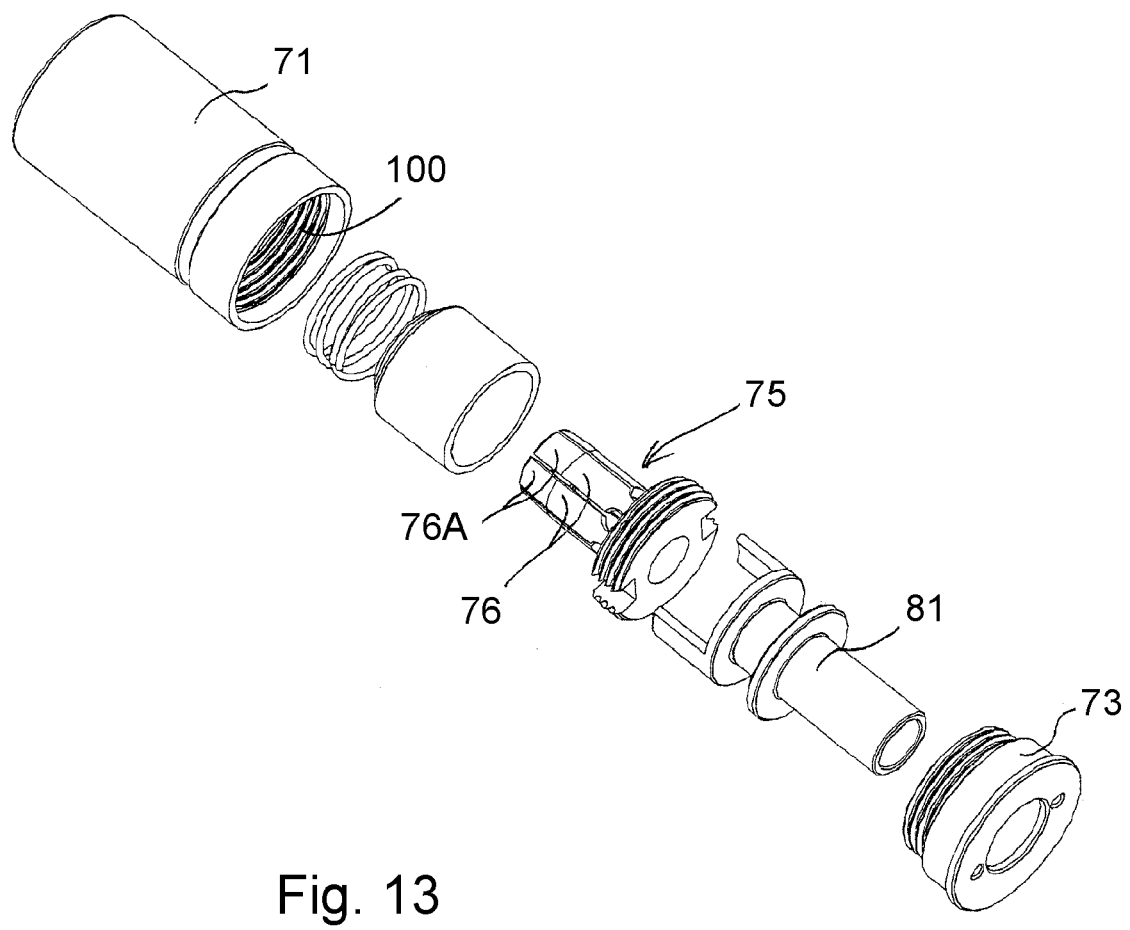
FIG. 13 is an exploded view of the discharge assembly of FIG. 12.
Figure 14:
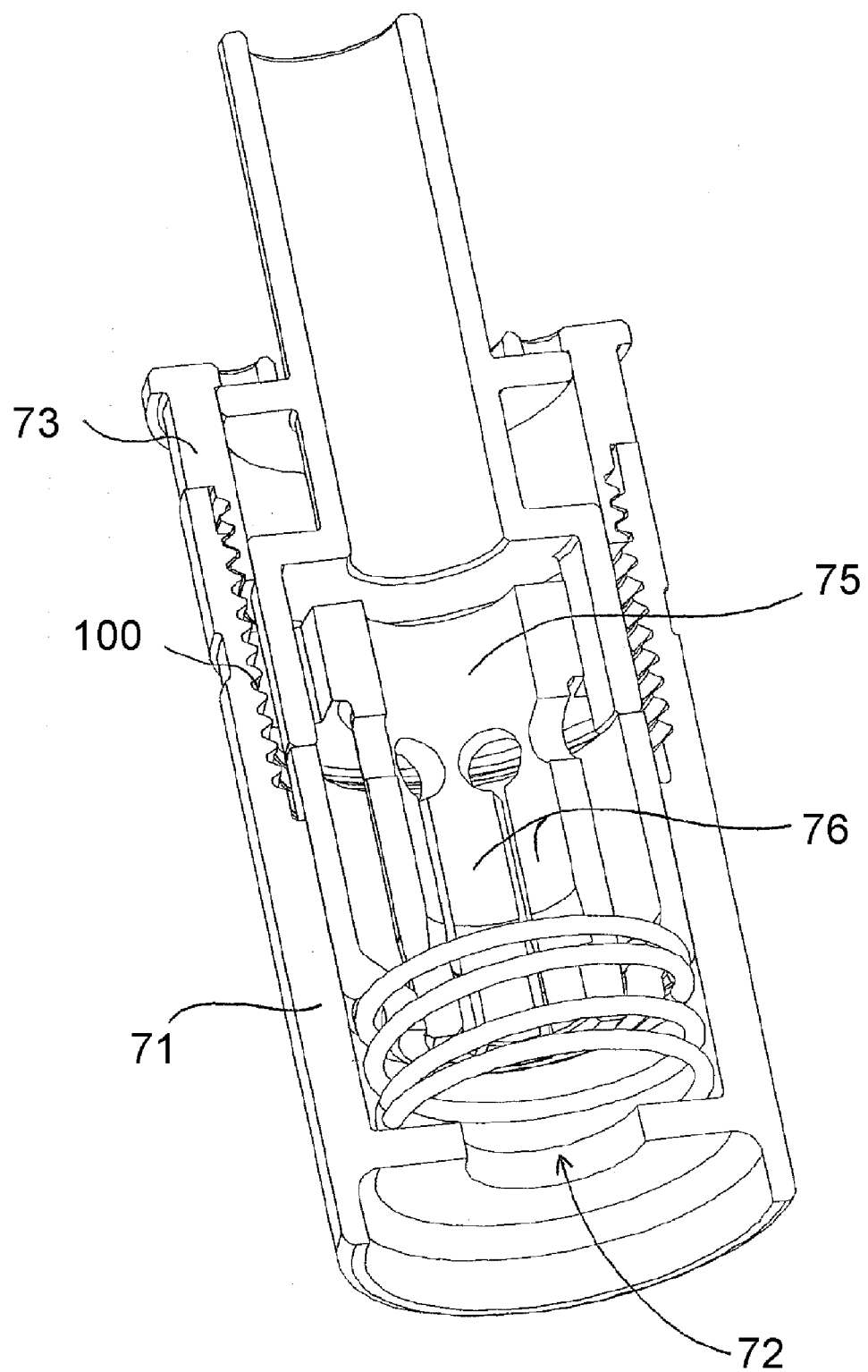
FIG. 14 is a cross-sectional perspective view of part of the discharge assembly.

As shown in FIG. 1, the injector comprises a nozzle assembly 20, a nozzle lock assembly 30, a housing assembly 40 and a firing assembly 50. Not visible in FIG. 1, as they are located inside the housing assembly 40, are a ram assembly 60 (see FIG. 10) and a discharge assembly 70 (see FIG. 12). Each of the assemblies will be described in more detail below with reference to the appropriate Figures.

In one embodiment of the injector, the nozzle is made from an opaque material and the nozzle lock assembly 30 extends far enough forward to obscure part of the nozzle assembly 20.

Nozzle Assembly

Figure 3:
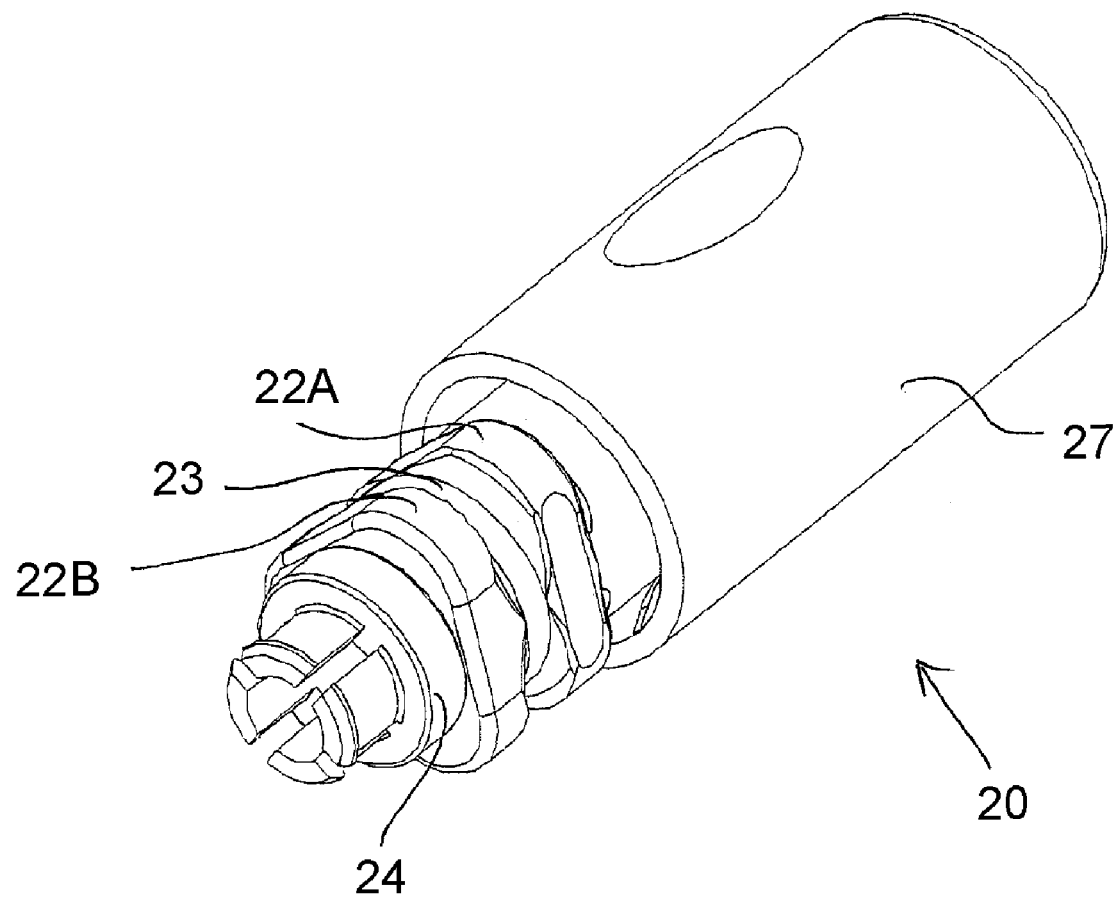
FIG. 3 is a perspective view of the nozzle assembly.
Figure 4:
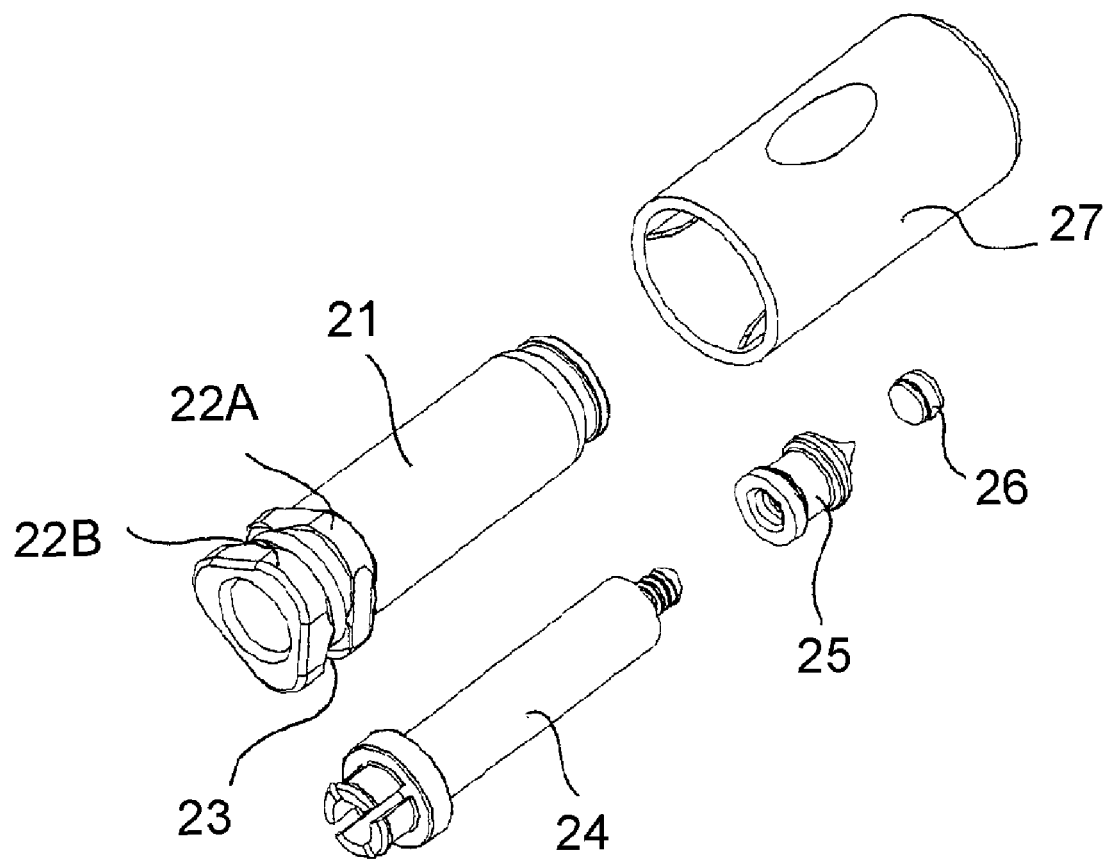
FIG. 4 is an exploded view of the nozzle assembly of FIG. 3.

The nozzle assembly 20 is shown in FIGS. 3 and 4. The assembly comprises a single hole nozzle 21 having two aligned substantially triangular formations 22A, 22B at the rearward end thereof. Between the triangular formations 22A, 22B is a slot 23. A piston 24 has a nozzle ram 25 press-fitted to, screw-threaded to or integrally-moulded with the forward end thereof and the piston/nozzle ram assembly fits within the bore of the nozzle 21. A cover seal 26 and a nozzle cover 27 can be press-fitted to the forward end of the nozzle 21, as shown in FIG. 3.

Nozzle Lock Assembly

Figure 5:
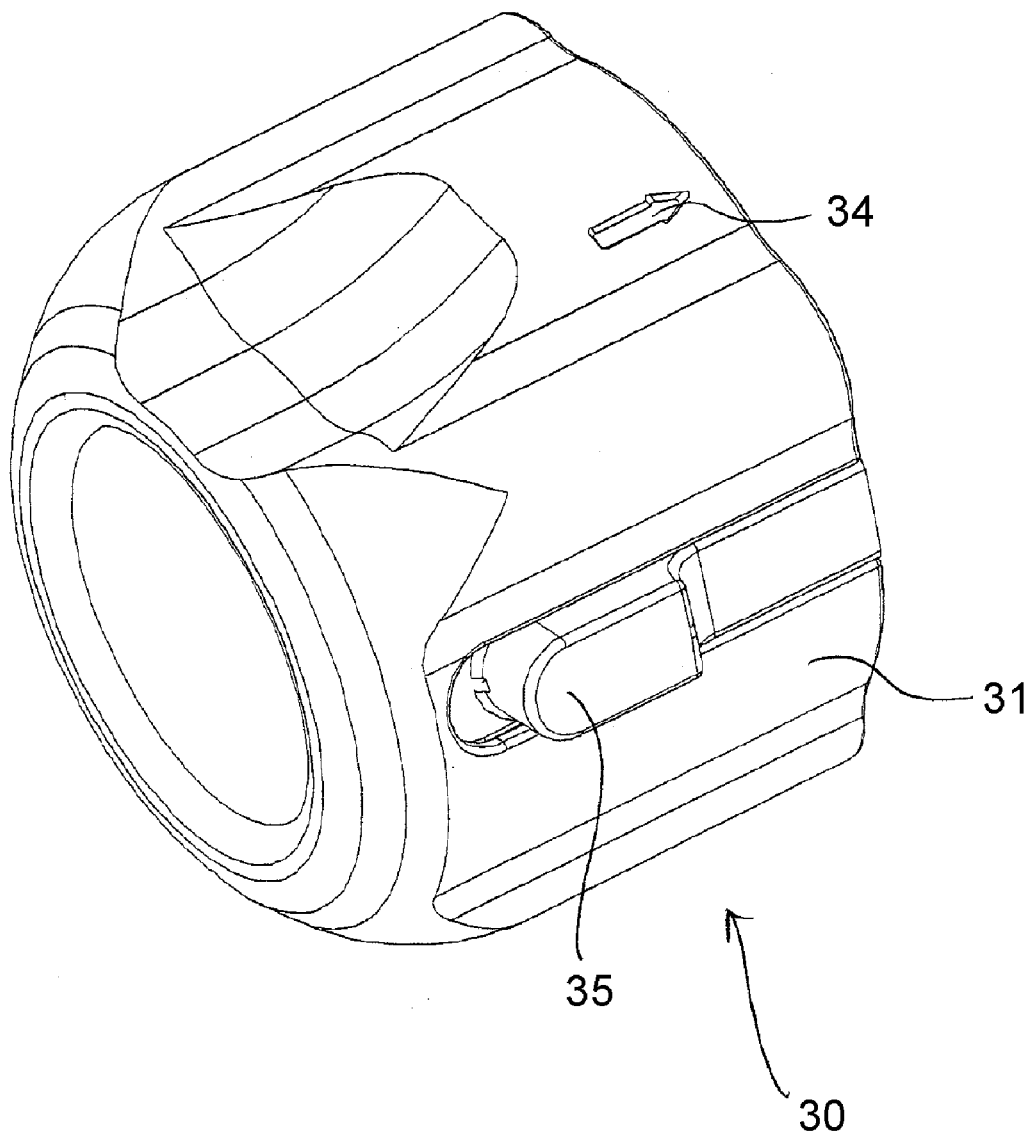
FIG. 5 is a perspective view of the nozzle lock assembly.
Figure 6:
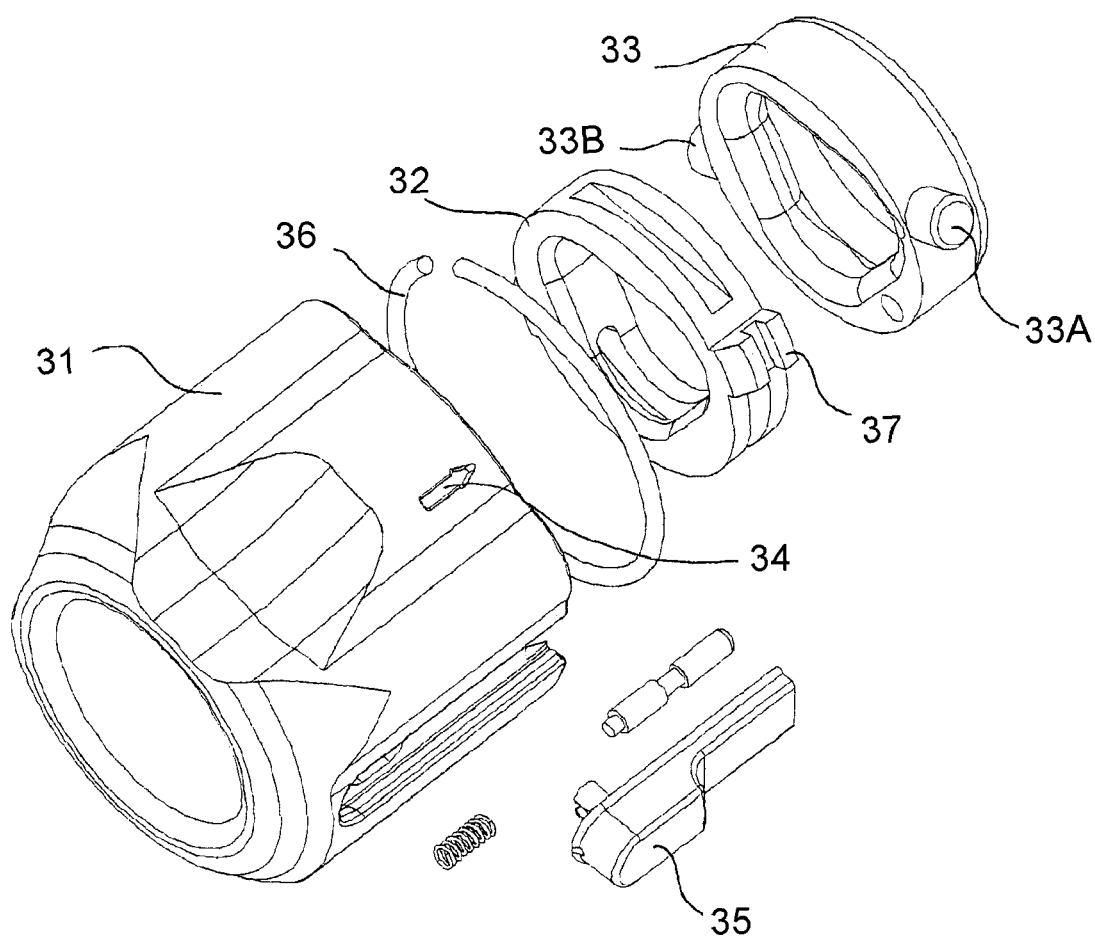
FIG. 6 is an exploded view of the nozzle lock assembly of FIG. 5.

The nozzle lock assembly 30 is shown in FIGS. 5 and 6. It provides a mechanism for releasably locking the nozzle assembly 20 to the rest of the injection device so that it is easy to remove and replace the nozzle assembly 20 at will. The nozzle assembly needs replacing, typically weekly, so it is advantageous to be able to do so quickly and easily.

The nozzle lock assembly includes a nozzle twist cap 31 which is used to actuate the nozzle lock. Inside the twist cap 31 is a retaining clip 32 which has a triangular aperture therethrough large enough for the triangular protrusions 22A, 22B of the nozzle assembly to pass through. The retaining clip 32 fixes the nozzle lock assembly 30 to the end of the injection device. Adjacent the retaining clip 32 is a lock yoke spacer 33 which has a similarly-sized triangular aperture therethrough. The lock yoke spacer 33 has two external protruding lugs 33A, 33B. These lugs engage in corresponding slots inside the twist cap 31 so that, upon twisting the twist cap 31, the lock yoke spacer 33 is driven in the same direction by the interaction between the lugs and corresponding slots. This enables the lock yoke spacer 33 to be moved between a first, open position in which its triangular aperture is aligned with that of the retaining clip 32 and a second, closed position in which the triangular apertures are offset by, for example, 60 degrees. The retaining clip 32 is fixed with respect to the rest of the injection device and hence does not twist when the twist cap is moved. An arrow 34 is marked on the twist cap 31 to indicate which position the lock yoke spacer 33 is currently in.

A spring clip 36 is provided which is held in place by one or more grips 37 on the retaining clip 32.

In order to insert the rearward end of the nozzle assembly 20 into the nozzle lock assembly 30, it is necessary for the lock yoke spacer 33 to be in the open position. The nozzle assembly can be inserted far enough that the lock yoke spacer 33 is located at the position of the slot 23 on the nozzle 21. Upon twisting the twist cap to the closed position, the lock yoke spacer 33 twists through 60 degrees so that it becomes out of alignment with the triangular protrusions 22A, 22B. This prevents withdrawal of the nozzle 21 from the nozzle lock assembly.

Optionally, a spring-biassed sliding switch 35 is provided on the twist cap 31, the switch 35 being biased into a position in which it prevents twisting of the twist cap. In order to twist the twist cap 31 to release the nozzle assembly, it is necessary to slide the sliding switch 35 forwardly.

In order to load medicament into the injection device of the present invention, a vial adaptor or cartridge is required which is compatible with the front end of the nozzle assembly 20. A suitable vial adaptor assembly is described below.

Figure 7:
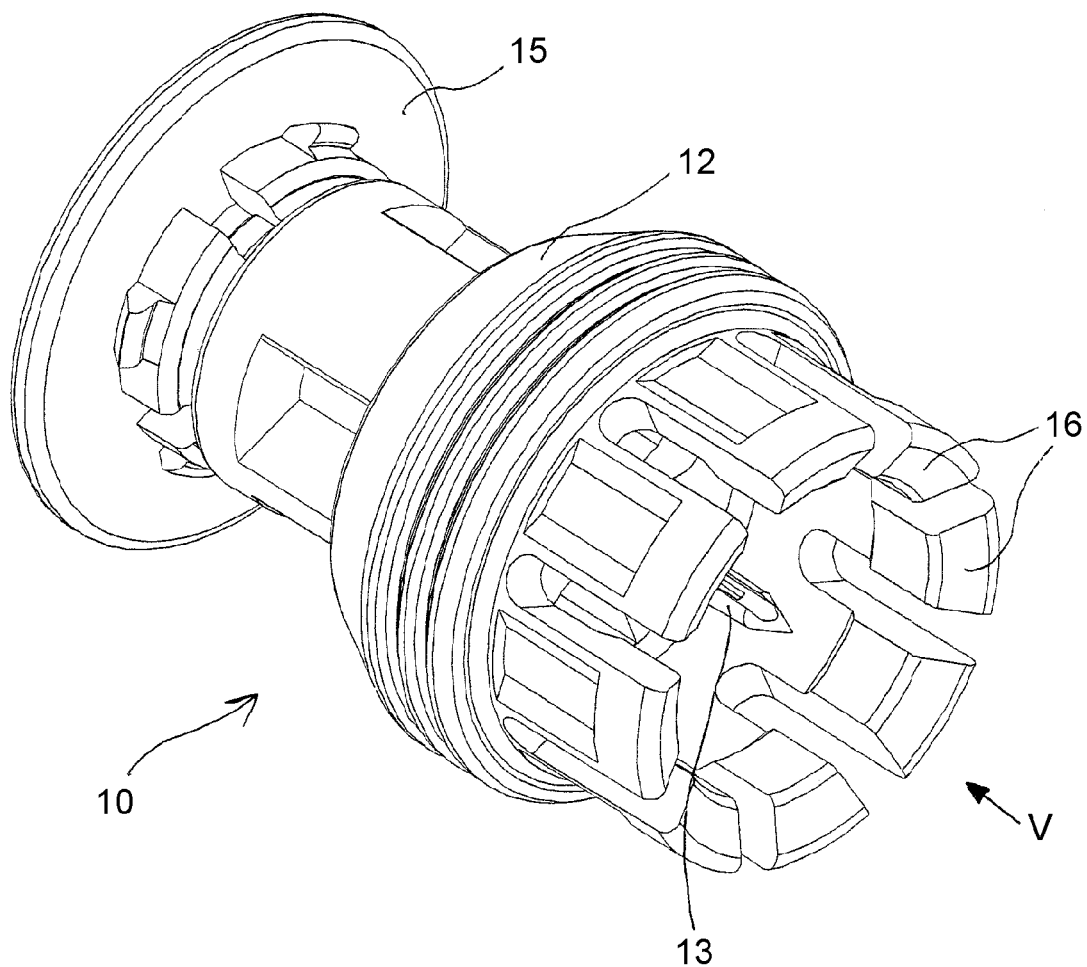
FIG. 7 is a perspective view of the vial adaptor assembly.
Figure 8:
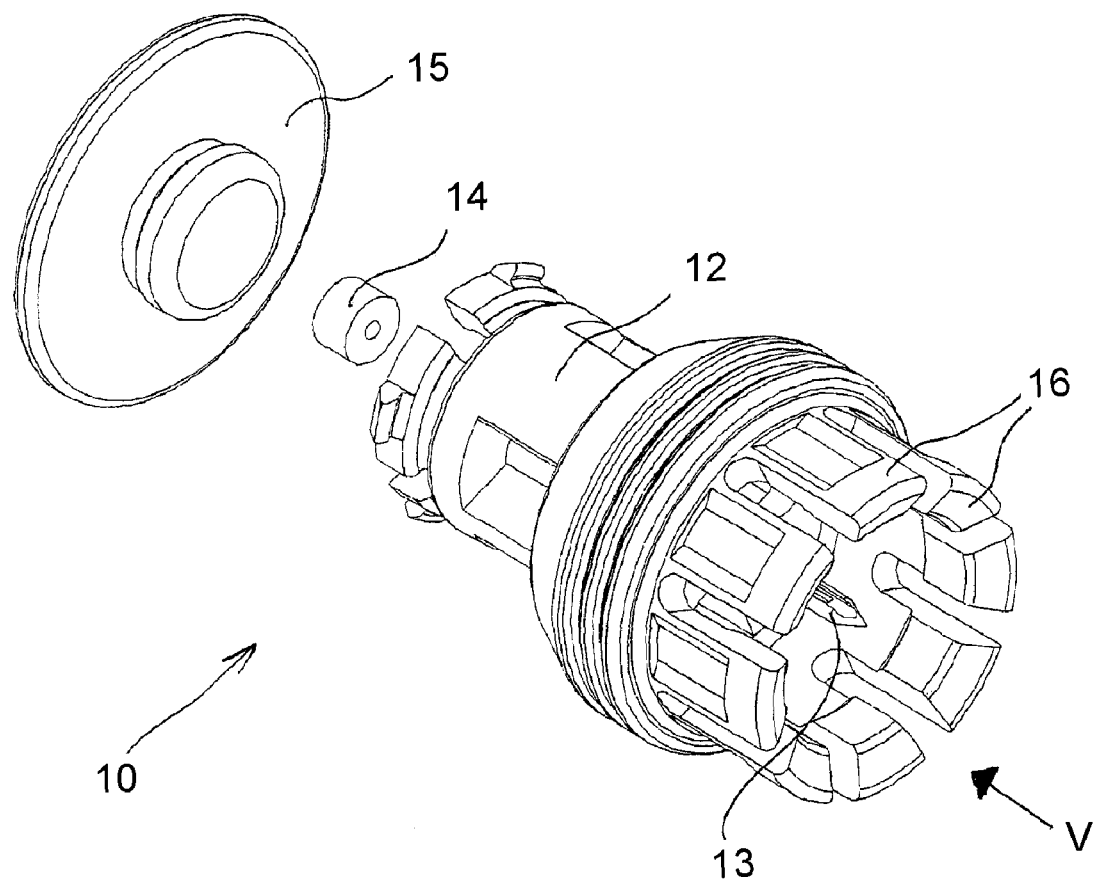
FIG. 8 is an exploded view of the vial adaptor assembly of FIG. 7.

A vial adaptor 10 is illustrated in FIGS. 7 and 8 which is designed to accept a standard sized proprietary medicament vial (for example a 10 ml medicament vial), to facilitate the loading of the medicament into the injector.

The vial adaptor is shown in exploded form in FIG. 8. The cartridge 10 has a housing 12 with an open rear end into which a vial (not shown) can be slid, in the direction indicated by arrow V, until it abuts a puncturing means 13. When the vial is placed inside the housing 12 and urged towards the puncturing means 13, this causes the end of the vial at the open rear end of the cartridge to be punctured by the puncturing means 13. Radially inwardly-biassed fingers 16 help grip the vial and hold it in position. A seal washer 14 and a bung 15 are fitted on the forward end of the housing to prevent egress of the medicament.

Upon removal of the bung 15, the vial adaptor is ready to be attached to the nozzle assembly 20 of the injector so as to enable medicament to be loaded into the injector.

Housing Assembly

Figure 9:
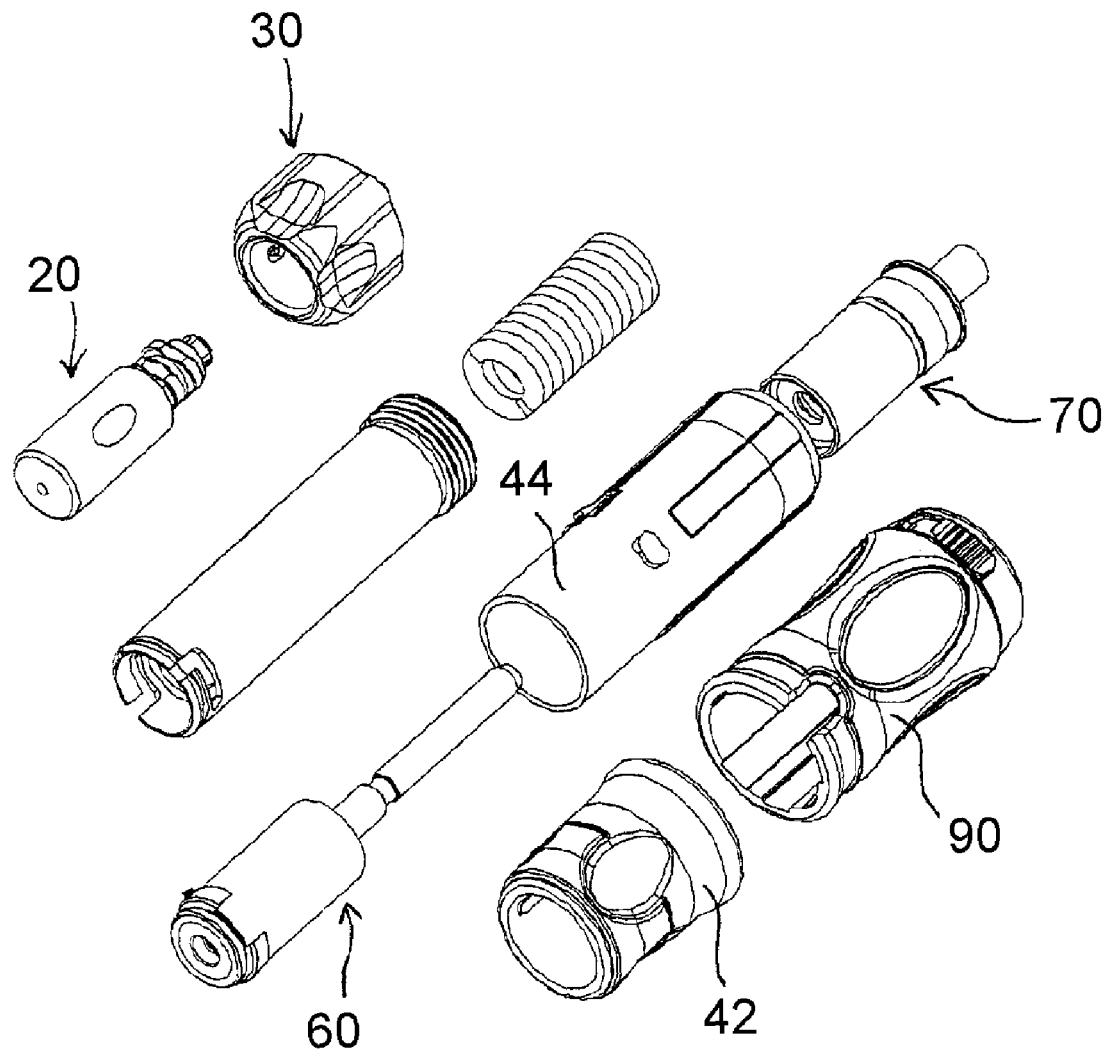
FIG. 9 is an exploded view, drawn to a smaller scale, of the injection device shown in FIG. 1.

Referring now to FIGS. 1 and 9, the housing assembly 40 comprises a two part housing; a front housing 42 and a rear housing 44. The two parts of the housing are rotatable with respect to one another. Most of the rear housing 44 is concealed by a shroud 90 which may have grip-improving surfaces or formations thereon to facilitate gripping by the user. The shroud 90 is axially moveable and is used to effect discharge of the injection device. Splines or other guide means may be provided on the outer surface of the rear housing 44 to guide the shroud 90 which moves over it.

Ram Assembly

The rear assembly 60 will now be described with reference to FIGS. 10 and 11. The ram 61 is the part which, in use, is urged forward in a rapid motion to move a plunger in order to expel medicament from the injection device.

At the forward end of the ram is a screw-threaded portion 62 which, when the ram assembly is assembled, co-operates with an internal screw-thread on a pressure nut 63. The forward end 64 of the pressure nut 63 is enlarged which defines the forwardmost limit of a chamber (described below) in which a main spring is situated. Relative movement of the pressure nut 63 and the ram 61 (by using the screw thread) changes the volume of the chamber and this is described in more detail below. A sleeve 65 forms the cylindrical wall of the chamber, as shown in FIG. 10. The pressure nut 63 is fixed with respect to the sleeve 65.

Figure 10:
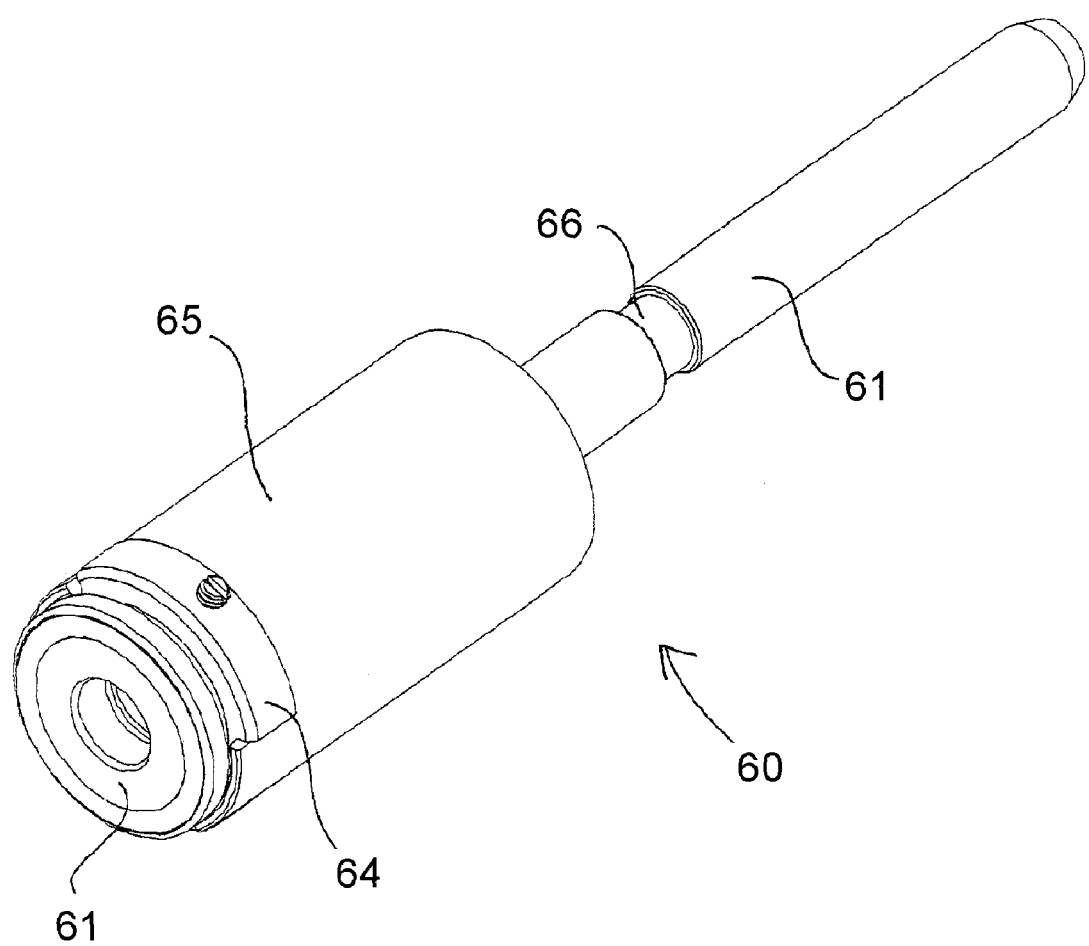
FIG. 10 is a perspective view of the ram assembly.
Figure 11:
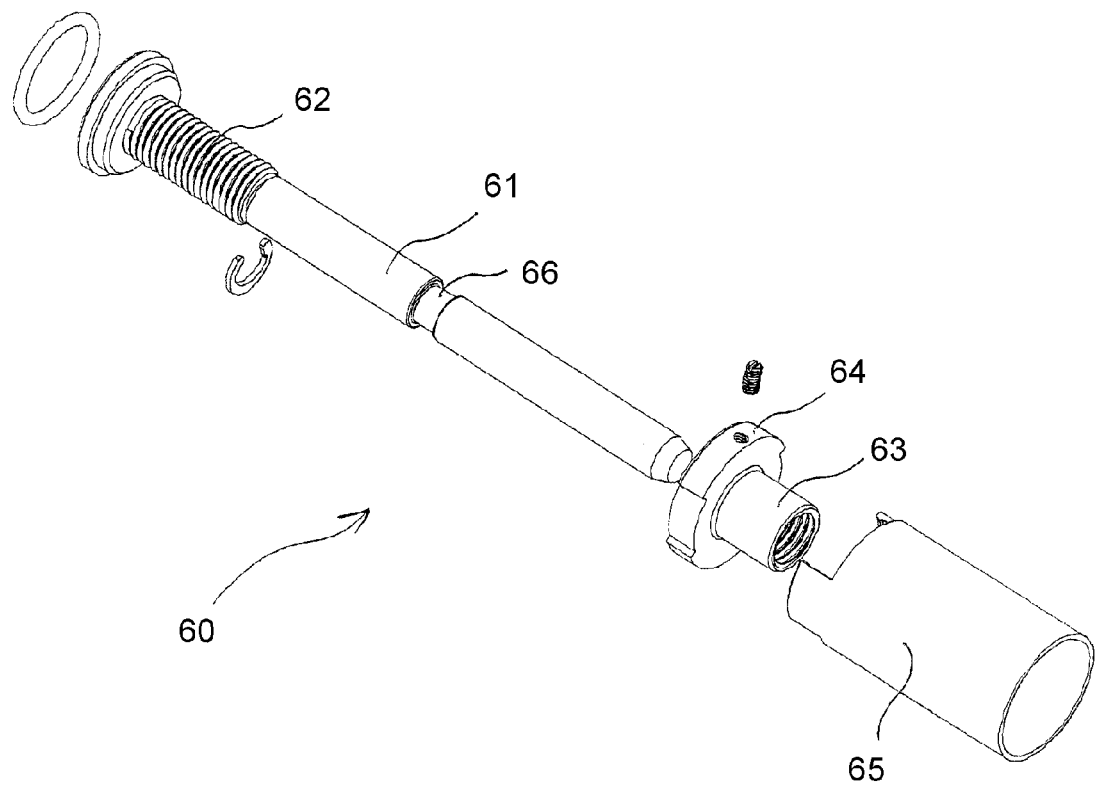
FIG. 11 is an exploded view of the ram assembly of FIG. 10.
Figure 15:
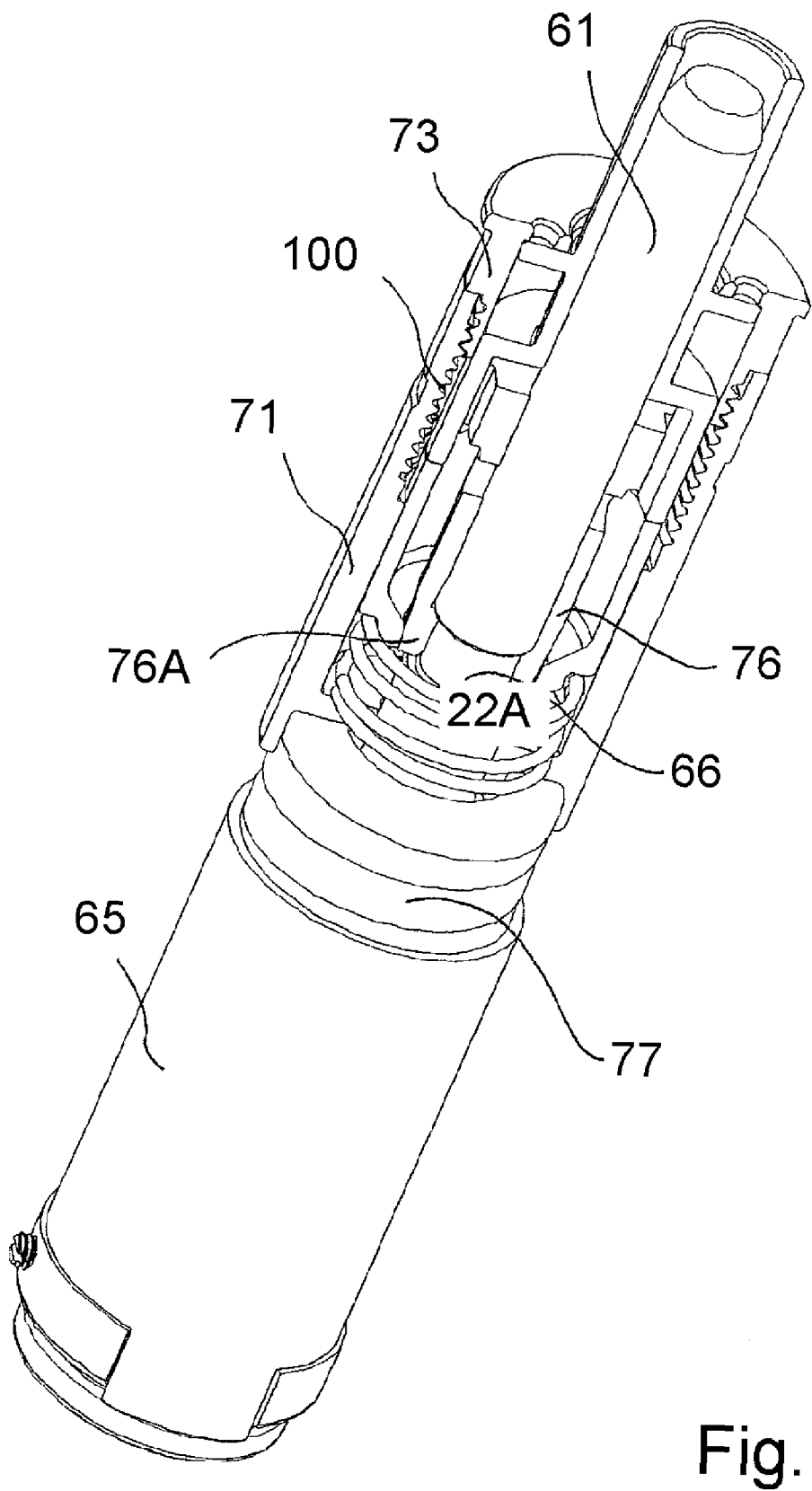
FIG. 15 is a perspective view, partly in cross-section of the assembled discharge and ram assemblies.

Finally, the ram 61 has an annular groove 66 which is as illustrated in FIGS. 10, 11 and 15 and described in more detail below.

Discharge Assembly

FIGS. 12-15 show the discharge assembly 70 which is used to lock the ram 61 in a position ready to fire (having compressed the main spring as described below) and then to release the spring-loaded ram at the desired moment upon actuation of a firing mechanism.

The discharge assembly 70 comprises a cylindrical housing 71 whose forward end is closed except for an aperture 72 of sufficient diameter to receive the rear portion of the ram. The rear end of the housing 71 is open and has an internal screw thread 100. A housing nut 73 screws into the rear end of the housing 71. The housing nut 73 has an aperture therethrough of sufficient diameter to receive the rear portion of the ram 61.

The discharge assembly includes a retention member, for example a collet 75, having a plurality of fingers 76 ("retention elements"), each having an enlarged head 76A. The enlarged heads 76A are suitably sized to fit into the groove 66 on the rear portion of the ram 61. This can be seen in FIG. 15. Also visible in FIG. 15 is the main spring 77.

Firing Assembly

The rearmost assembly in the injection device is the firing assembly 50, illustrated in FIGS. 1 and 16-18. The firing assembly includes a shroud 90 which has protrusions or a textured surface thereon. In use, as described below, the user grips the shroud 90, can rotate it with respect to the front housing of the device and can move it axially in order to fire the device. The protrusions or textured surface aid gripping by the user.

The firing assembly also includes a safety lock facility which prevents inadvertent firing of the injection device.

Figure 16:
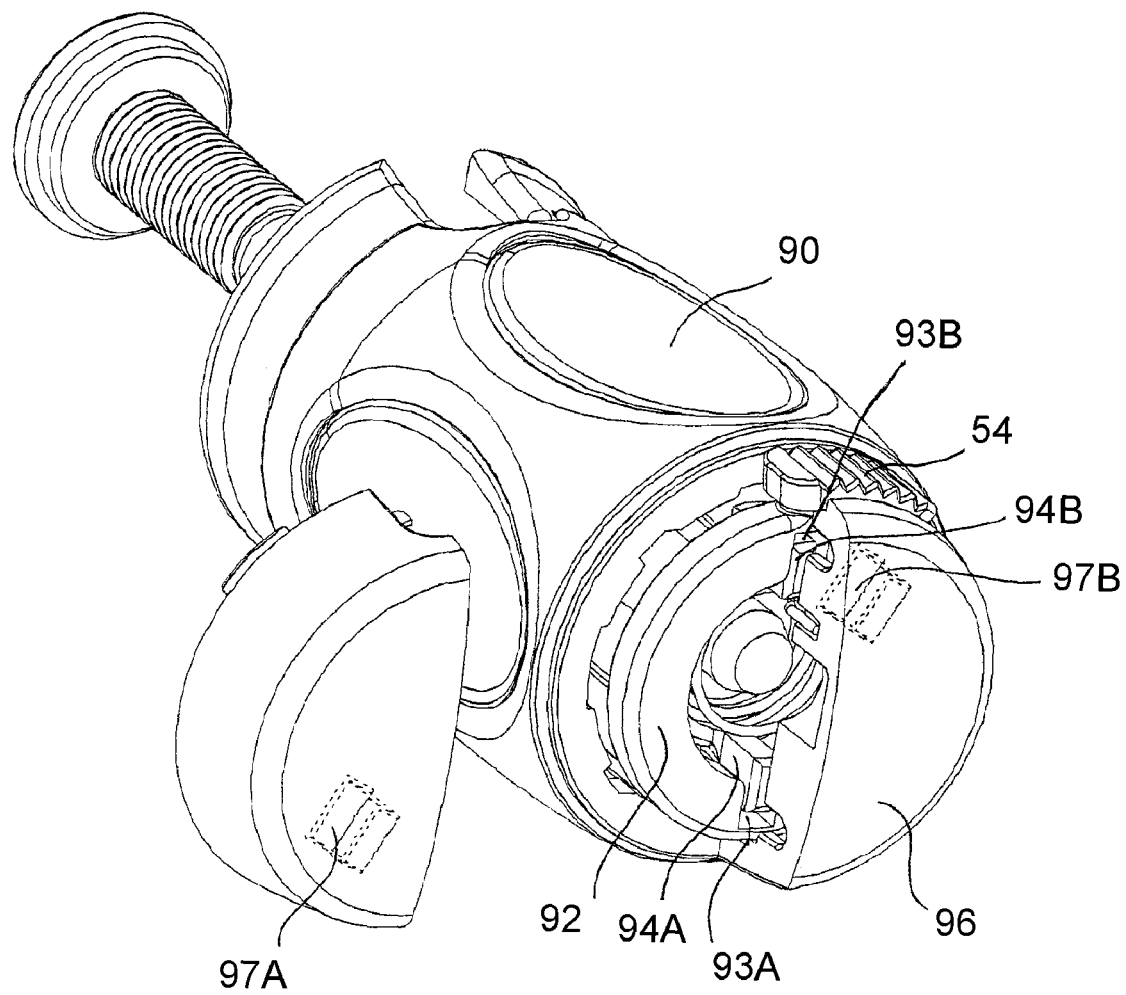
FIGS. 16-18 are perspective views of the firing assembly.
Figure 17:
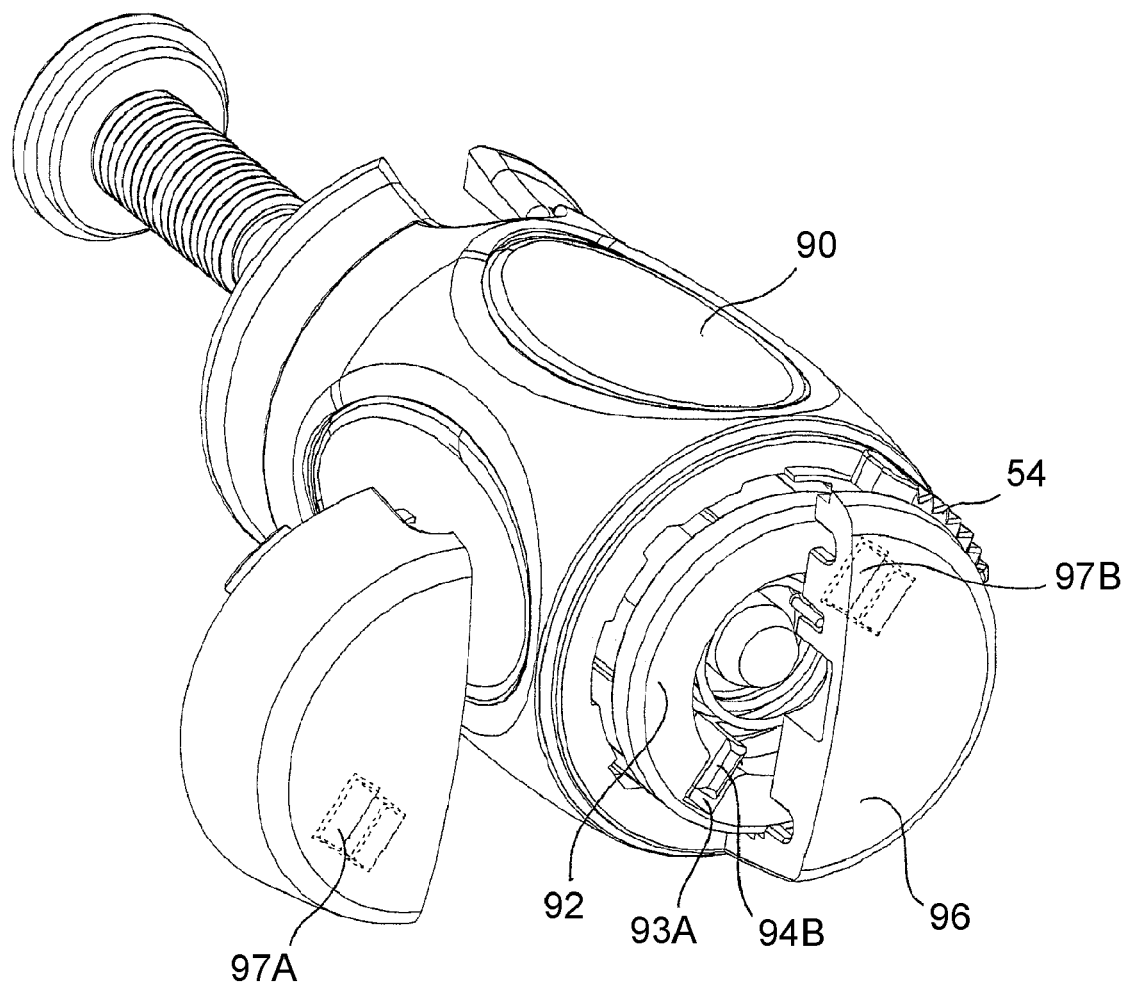
Figure 18:
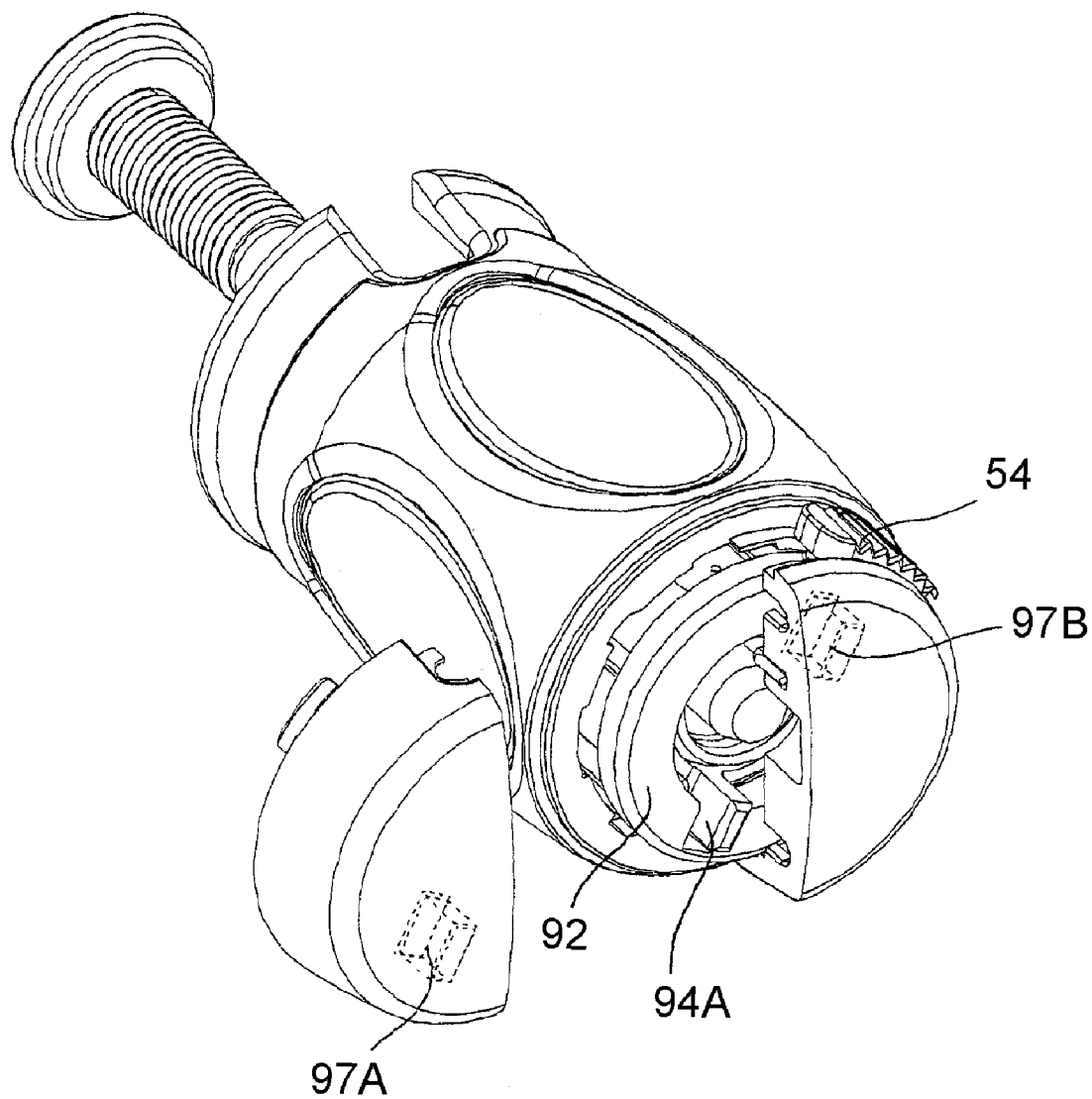

The firing assembly is illustrated in FIGS. 16-18. The shroud 90 is provided with a sliding switch 54 which, when slid from the position illustrated in FIG. 16 to the position illustrated in FIG. 17, engages with a drive plate 92 which causes corresponding rotation thereof.

The drive plate 92 includes two diametrically opposed slots 93A, 93B. An annular ring has two axially-extending tabs 94A, 94B which locate within the slots 93A, 93B. This means that, when the drive plate 92 is caused to rotate (by sliding of the switch 54), the tabs 94A, 94B are also forced to rotate by the drive plate 92.

Figure 19:
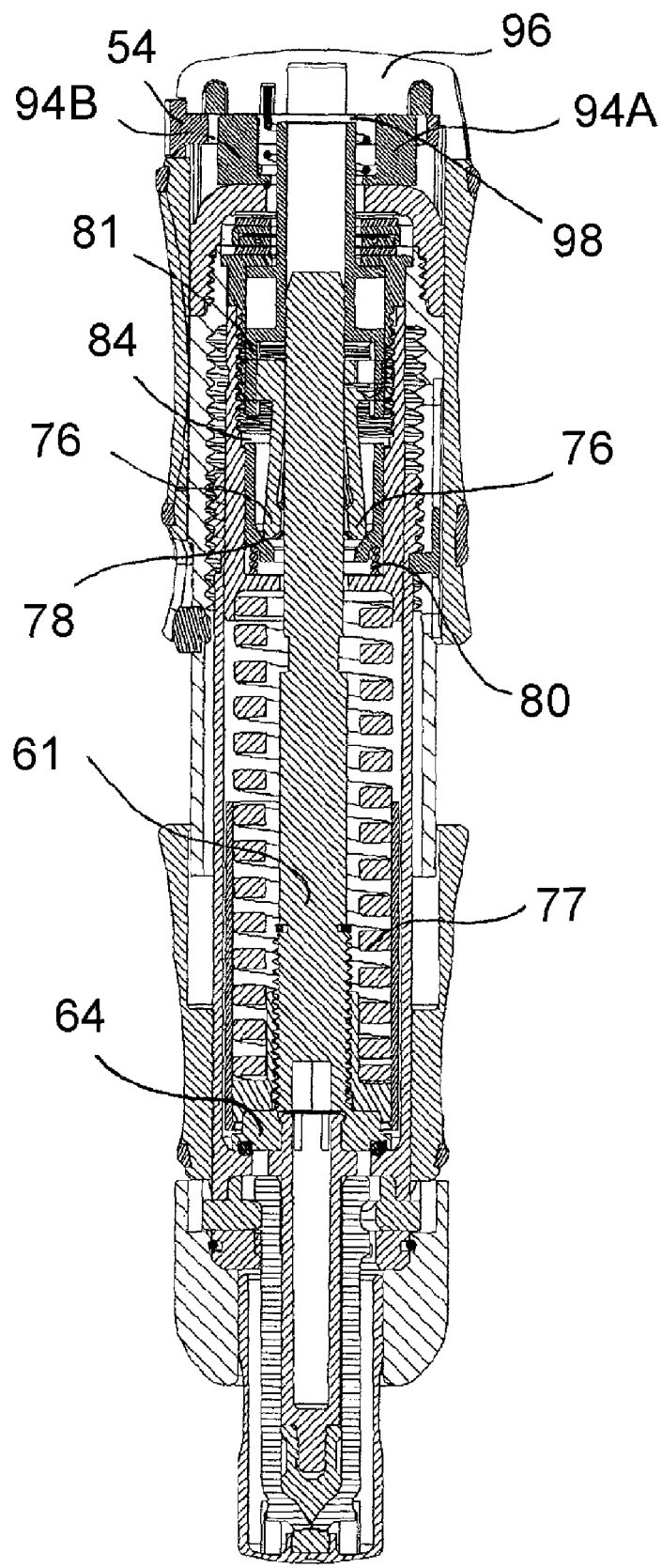
FIG. 19 is a longitudinal cross-sectional view of the injection device, in a just-discharged condition.

The annular ring containing the tabs 94A, 94B is biassed rearwardly by a spring 95 (shown in FIG. 19 et seq). The tabs are normally prevented from moving rearwardly because they abut an endcap 96. However, the endcap 96 is provided with two diametrically opposed recesses 97A, 97B on the interior surface thereof. The recesses are large enough to accommodate the tabs if they are correctly aligned therewith. Therefore the tabs 94A, 94B are moveable between two axial positions; one wherein they abut the endcap 96 and another wherein they can move axially-rearwardly to fit into the recesses 97A, 97B. The tabs can be rotated between these two positions by sliding of the switch 54.

The key stages in the basic operation of the injection device will now be described in turn. FIG. 19 shows the injection device in a just-discharged condition, i.e. ready to be prepared for firing again. With reference to FIG. 19, it can be seen that the ram 61 is in a forward position with its forward end 64 abutting the housing. The main spring 77 is at its maximum extent, having just been discharged. The collet fingers 76 are radially-spread and a collet lock sleeve 78 is positioned forward of the collet fingers 76, with a secondary spring 80 being compressed. Although the secondary spring 80 is compressed, rearward axial movement of the collet lock sleeve 78 is prevented by its abutment against the collet fingers 76. An annular gap 84 is present between the collet lock sleeve 78 and the release fingers 81. Note that the tabs 94A, 94B abut the endcap 96 and that there is a gap 98 between the endcap 96 and the rear of the release fingers 81.

Loading a Vial into the Vial Adaptor Assembly

Referring back to FIGS. 7 and 8, firstly, the end cap on a vial of the desired medicament is pulled off. The vial is pushed into the open rear end of the housing 12. As the vial is urged against puncturing means 13, the end wall of the vial is punctured. The vial bung 15 prevents egress of the medicament from the vial at this stage.

Priming the Spring

Figure 20:
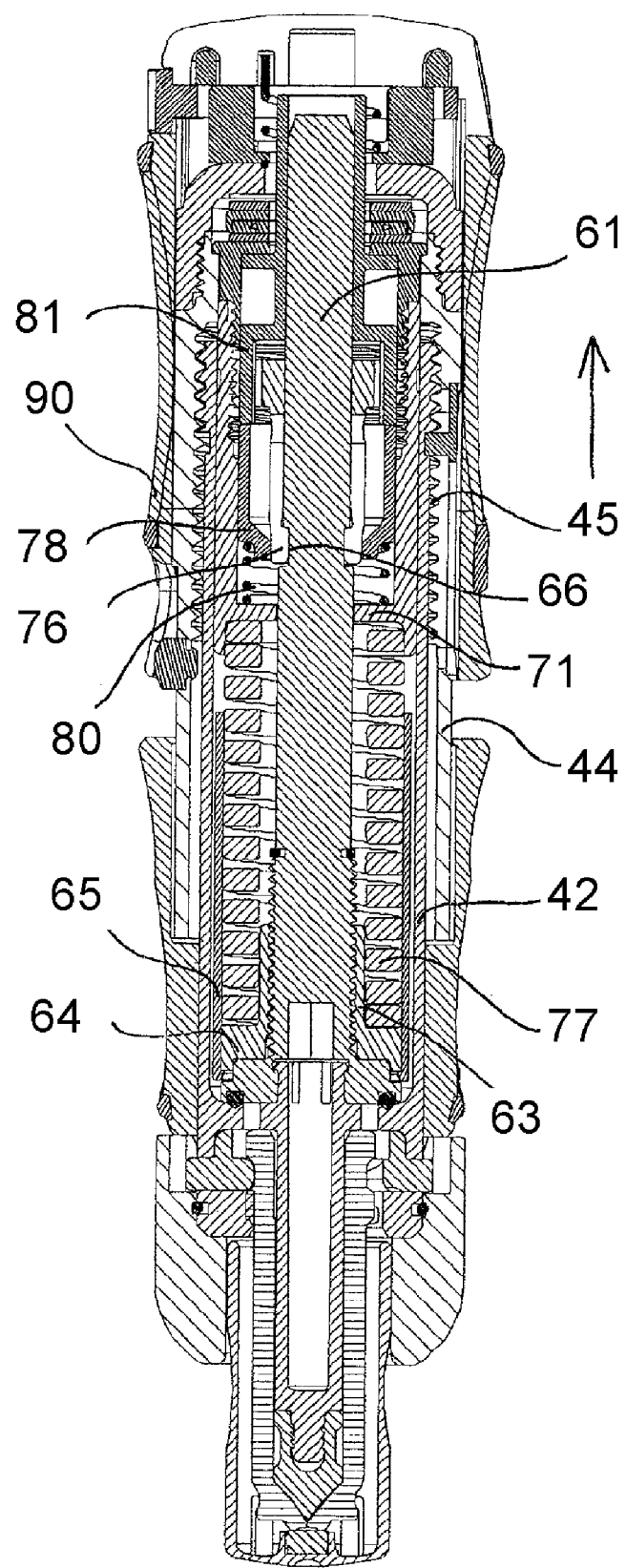
FIG. 20 shows the injection device of FIG. 19 with the spring primed.

Before a dose of medicament can be loaded, it is necessary to prime the main spring 77 so that the injection device is ready to fire. Referring to FIG. 20, the main spring 77 is housed within a chamber having a cylindrical wall formed by sleeve 65 (see FIGS. 20 and 10). The forward end of the chamber is defined by the forward end 64 of the pressure nut 63. The rearward end of the chamber is defined by the forward end of the housing 71 (see FIGS. 20 and 14).

The front housing 42 is rotatable with respect to the rear housing 44. Referring again to FIG. 20, when the rear housing 44 is held stationary (by gripping the shroud 90), and the front housing 42 is rotated in a clockwise direction (when viewed from the rear end of the injection device), the screw thread 45 at the rear end of the front housing advances rearwardly along a corresponding screw thread on the rear housing in the direction indicated by the arrow in FIG. 20. Since the discharge assembly housing 71 is fixed with respect to the central housing, this causes a shortening of the chamber containing the main spring as the front housing moves rearwardly, thus compressing the main spring 77.

FIG. 20 shows the situation in which the chamber has been reduced to its minimum length and the spring 77 is fully compressed. In this position, the enlarged heads 76A of the collet 75 drop into the groove 66 on the rear portion of the ram 61. The collet fingers 76 have a tendency to spring radially inwardly toward one another which is why they readily drop into the groove 66 when they reach this portion of narrowed diameter. However, the compressive force stored in the main spring 77 means that the ram has a great tendency to move axially forward (which would force the collet fingers 76 radially apart). The location of the collet fingers 76 in groove 66 is not sufficient alone to resist this. Therefore a collet lock sleeve 78 is employed. The collet lock sleeve 78 is biassed rearwardly by a secondary spring 80 which is under compression. When the collet fingers 76 drop into groove 66, the collet lock sleeve 78 moves rearwardly sufficient to transmit rearward force to the shroud 90 so that the shroud is firmly positioned ready for actuation. The collet lock sleeve 78 engages the enlarged heads 76A of the collet fingers. This has the effect of preventing further rearward movement of the collet lock sleeve 78 and also prevents radial movement of the collet fingers which therefore remain engaged in the groove 66. The gap 84 (see FIG. 19) which was present between the collet lock sleeve 78 and the release fingers 81 has closed. The ram is now held in a fixed position relative to the rear housing 44. The main spring is now primed and the injection device is ready for a dose of medicament to be loaded.

Loading a Dose of Medicament into the Nozzle

The vial bung 15 is removed from the loaded vial adaptor assembly 10, which is then pushed onto the nozzle assembly 20 on the forward end of the assembled injection device (FIG. 1). The medicament in the vial is now in communication with the nozzle 21.

With reference to FIG. 20, although the spring has been primed, an injection cannot yet be delivered because the forward end of the ram 61 abuts the front housing 42 and the dose of medicament has not yet been loaded. It is necessary to retract or wind back the ram in order to load the medicament and to get the injection device into a condition ready for firing. This is achieved by anti-clockwise rotation (when the injection device is viewed from the rear) of the front housing 42 with respect to the rear housing 44.

Figure 21:
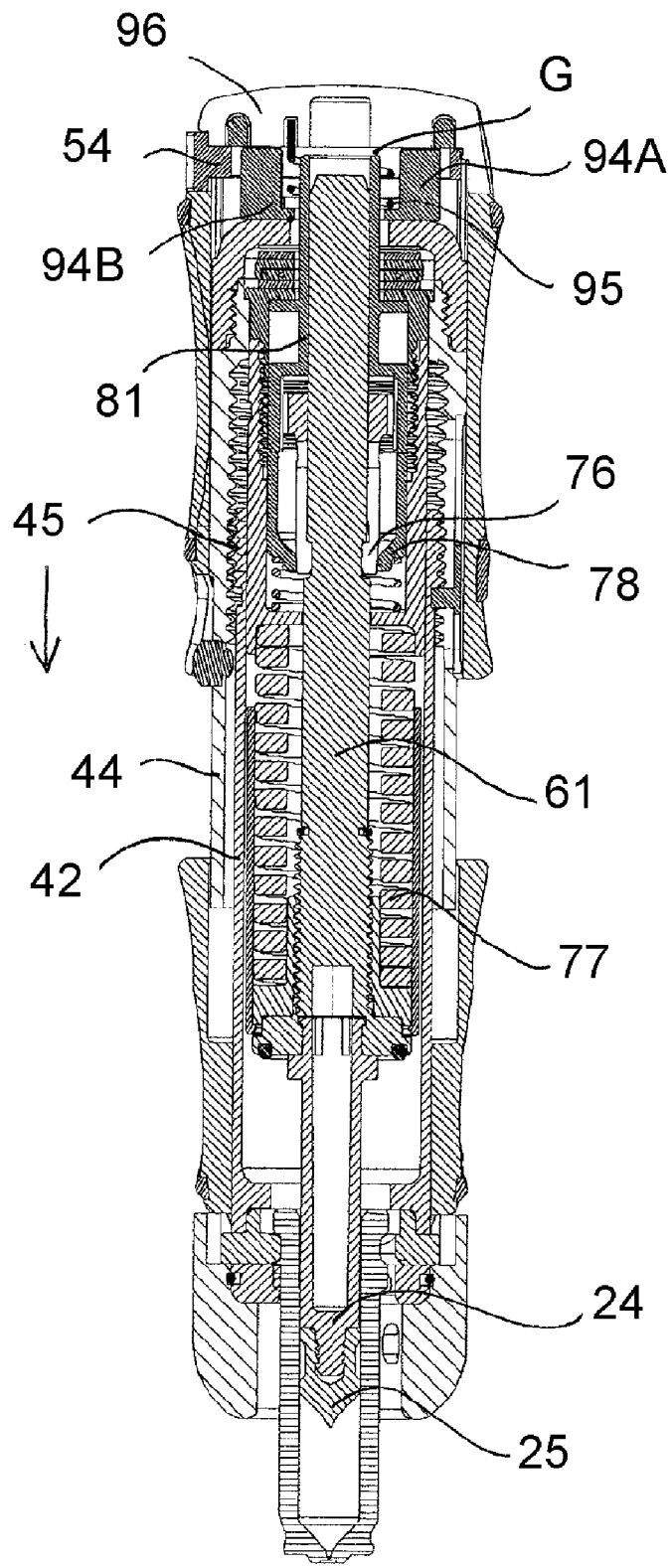
FIG. 21 shows the injection device of FIG. 19 ready to be discharged.

With reference to FIG. 21, this anti-clockwise rotation causes the screw thread 45 at the rear of the front housing 42 to advance forwards in the direction indicated by the arrow (with respect to the corresponding screw thread on the rear housing 44). The chamber in which the main spring 77 is situated does not get longer because the ram 61 is held in a fixed position with respect to the rear housing 44 by the collet 76 and collet lock sleeve 78. Instead, the front housing 42 advances forwards, leaving the whole ram assembly, main spring and discharge assembly fixed with respect to the rear housing 44. This creates a space at the forward end of the injection device into which the ram can be driven when the device is discharged.

The effect of this is to cause the piston/nozzle ram 24, 25 to retract away from the nozzle aperture, drawing the medicament into the nozzle. A dose indicator indicates, through a window 46 (see FIG. 1) in the main housing assembly 40, the volume of the medicament dose loaded into the nozzle. In addition or alternatively, an audible dose indicator could also be provided. When the desired dose has been loaded into the nozzle, the vial assembly 10 can be removed,

Releasing Safety Lock

As illustrated in FIG. 21, the injection device cannot be fired because the tabs 94A, 94B abut the endcap 96 so that there is a gap G which prevents transmission of axial pressure from the endcap 96 to release fingers 81. It is therefore necessary to release the safety lock by sliding switch 54 in order to close gap G. Sliding the switch 54 causes the tabs 94A, 94B to be rotated into alignment with the recesses 97A, 97B in the endcap. This position is illustrated in FIG. 17.

Figure 22:
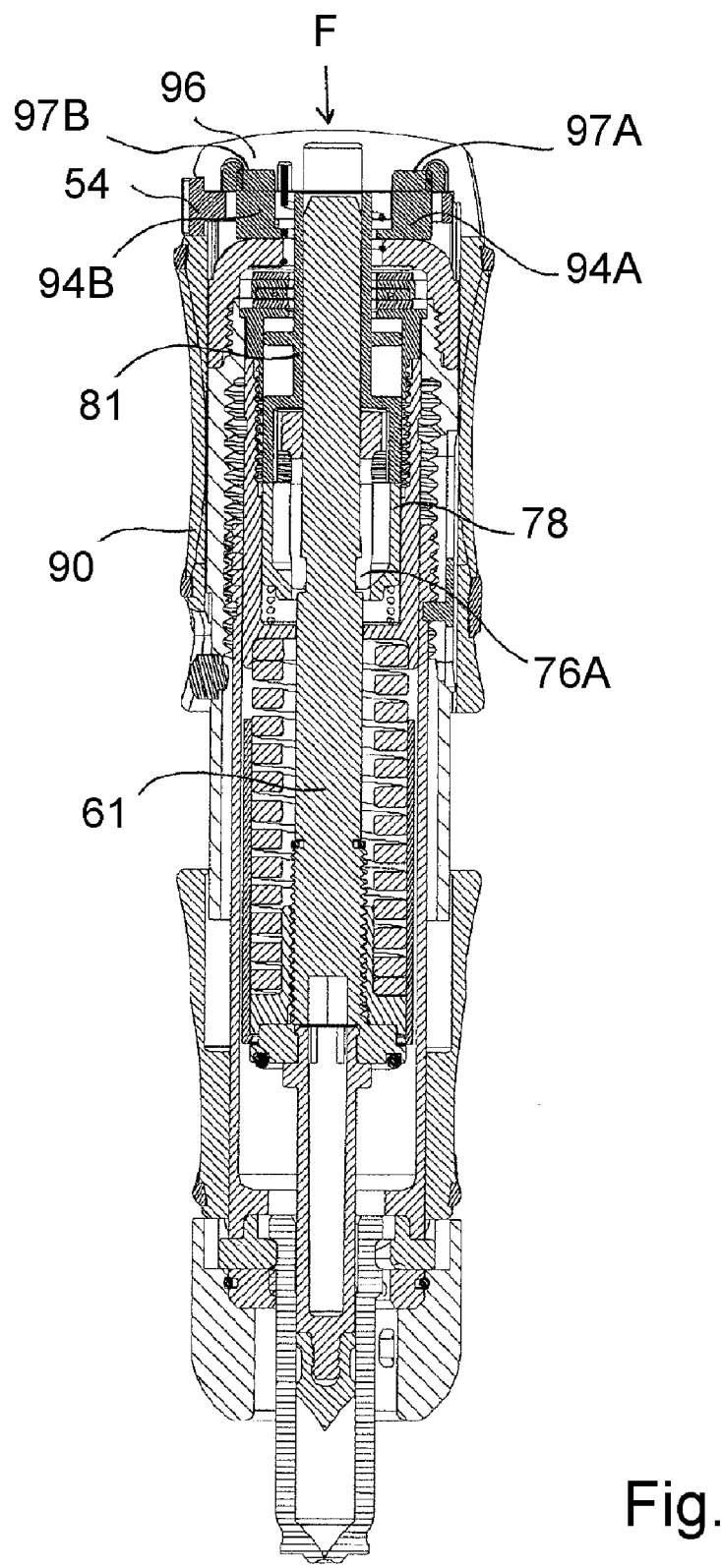
FIG. 22 shows the injection device of FIG. 19 at the instant of applying pressure to the shroud.

Now the tabs 94A, 94B are able to move axially-rearwardly into the recesses 97A, 97B as they are biassed by the spring 95, closing the gap G. This position is illustrated in FIGS. 18 and 22.

Firing the Injection Device

When the injection device is ready to be discharged (or "fired"), as is described in more detail below, the device is simply held against the patient's skin at the desired injection site. Usually, the device is brought to the injection site and held in contact there by grasping the shroud 90. The device has the advantage that the user need not move his/her hand position from grasping the device in order to press a button or other actuating means elsewhere on the device. The device can be discharged simply by applying downward force F to the shroud 90 whereby a slight axial movement towards the patient's skin will fire the device. The device is thus resistance-sensitive in that the downward axial force is resisted by the skin of the patient until sufficient force is applied to trigger the device. The force required depends on, among other factors, the properties of the secondary spring 80 and the spring 95 (described below).

Figure 23:
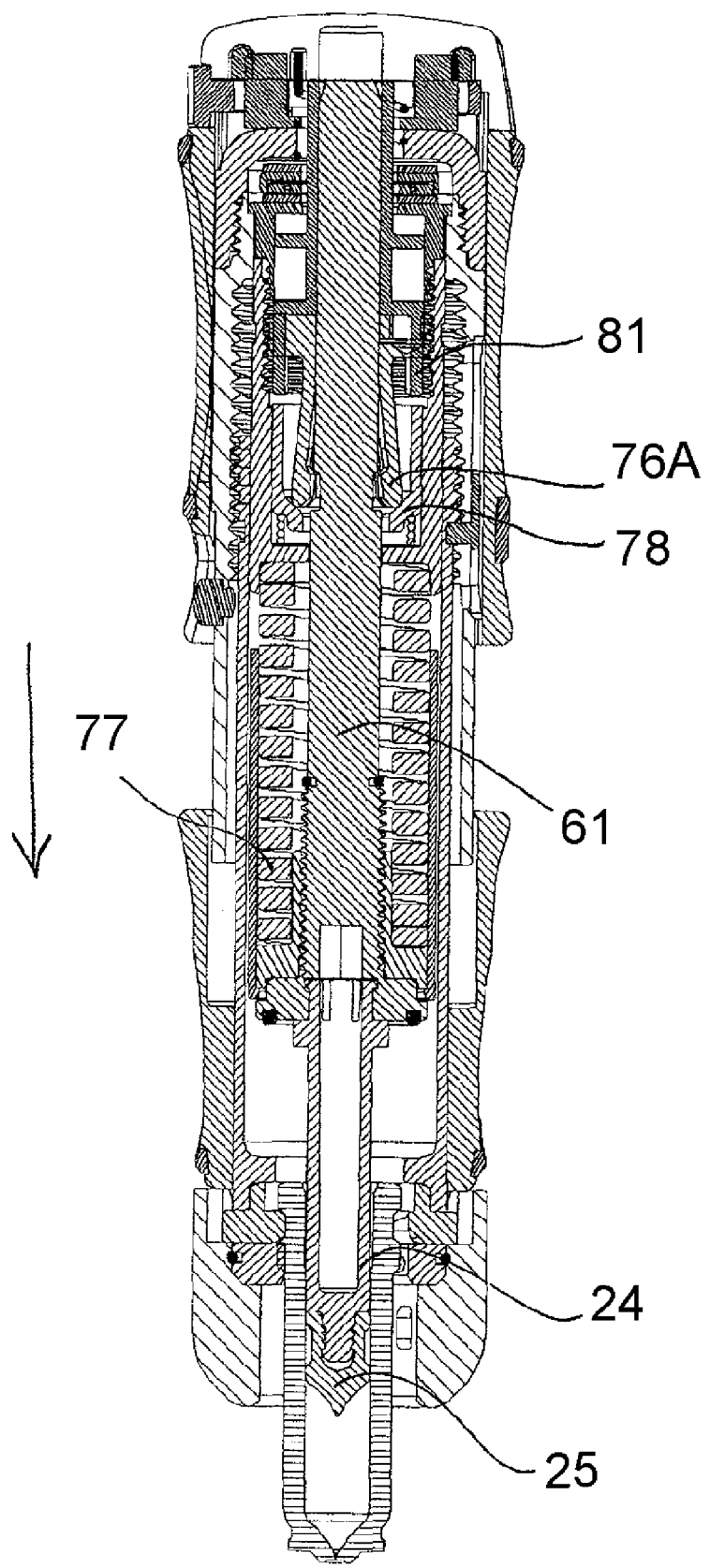
FIG. 23 shows the injection device of FIG. 19 part-way through release of the collet fingers from the groove on the ram.
Figure 24:
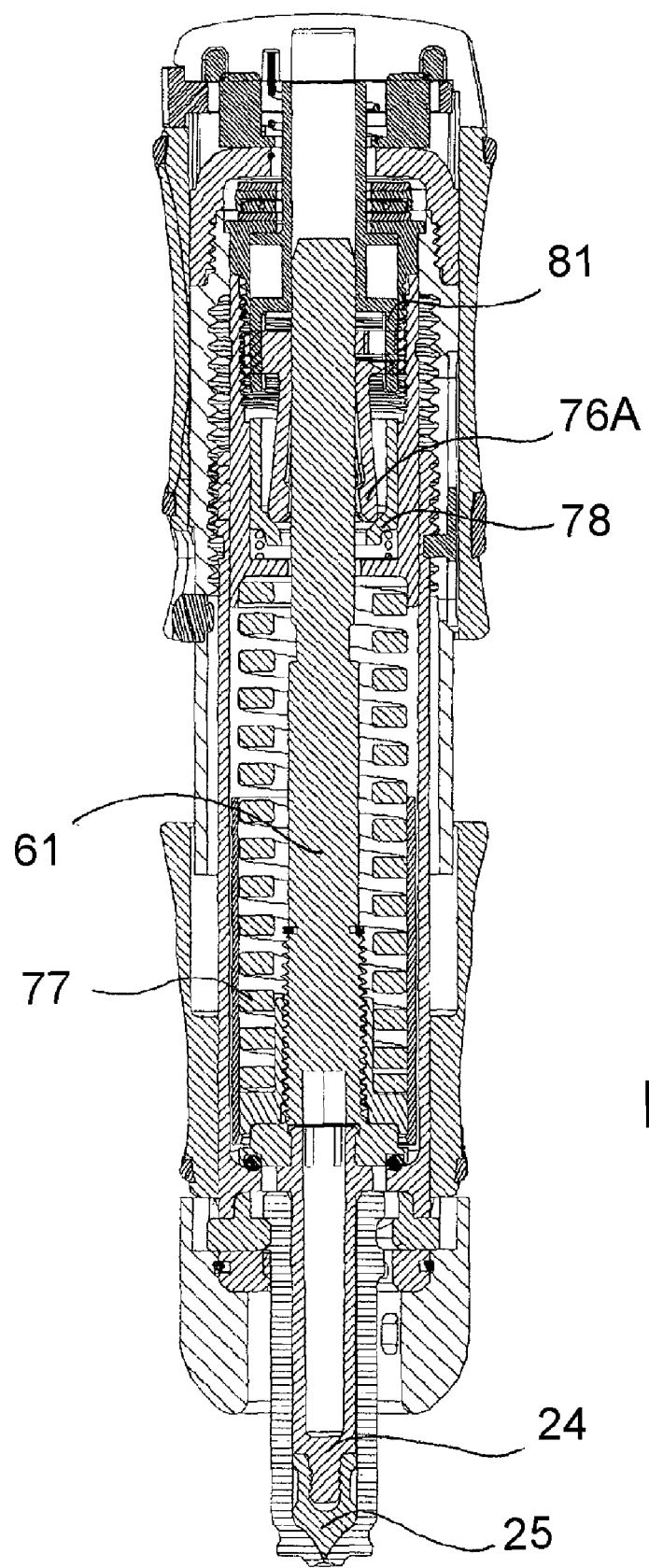
FIG. 24 shows the injection device of FIG. 19 with the collet fingers fully released from the groove on the ram.

With the injection device held against the patient's skin at the desired injection site, axial force F is applied to the shroud 90 and hence to endcap 96 which brings the endcap 96 into engagement with the rear of the release fingers 81. This applies a forward force to the release fingers 81 which push forwardly against the collet lock sleeve 78 which, in turn, causes the collet lock sleeve to disengage from the tapered enlarged heads 76A of the collet 75. The slightest disengagement of the collet lock sleeve 78 from the collet allows the stored force in the main spring 77 to cause the collet fingers 76 to move radially-outward out of the groove 66 which releases the ram (as shown in FIG. 23). Once free to move, as illustrated in FIG. 23, the ram is driven forcefully forward by the main spring 77. The front portion of the ram 61 drives the piston 24 and nozzle ram 25 into the nozzle, where the medicament is located, causing the medicament to be ejected from the nozzle and into the patient. Having been fixed, the injection device is in the condition illustrated in FIG. 24.

Adjusting the Firing Force

The injection device also includes a facility for adjusting the force with which the injection device fires a medicament into the patient (the "pressure adjustment" facility).

The firing force of the injection device is determined by the properties of the main spring 77, in particular the degree to which it is compressed before the device is fired. There is sometimes a desire to adjust the firing force of an injection device since, for example, in certain patients a powerful device may causes bruising or trauma at the injection site. Conventional needleless injection devices can be adjusted by the provision of "comfort rings" which limit the force which can be stored in the main spring. However, the injection device needs to be disassembled in order to insert the comfort rings and this brings the risk of injury caused by inadvertent firing and/or incorrect reassembly of the device. The injection device described herein enables the firing force to be adjusted without the need to take apart the device.

The injection device of the present invention includes an integral mechanism for adjusting the firing force. For safety reasons, it is only possible to adjust the firing force when the injection device is in the condition illustrated in FIG. 19 i.e. fully discharged, with the ram 61 fully-forward.

Figure 25:
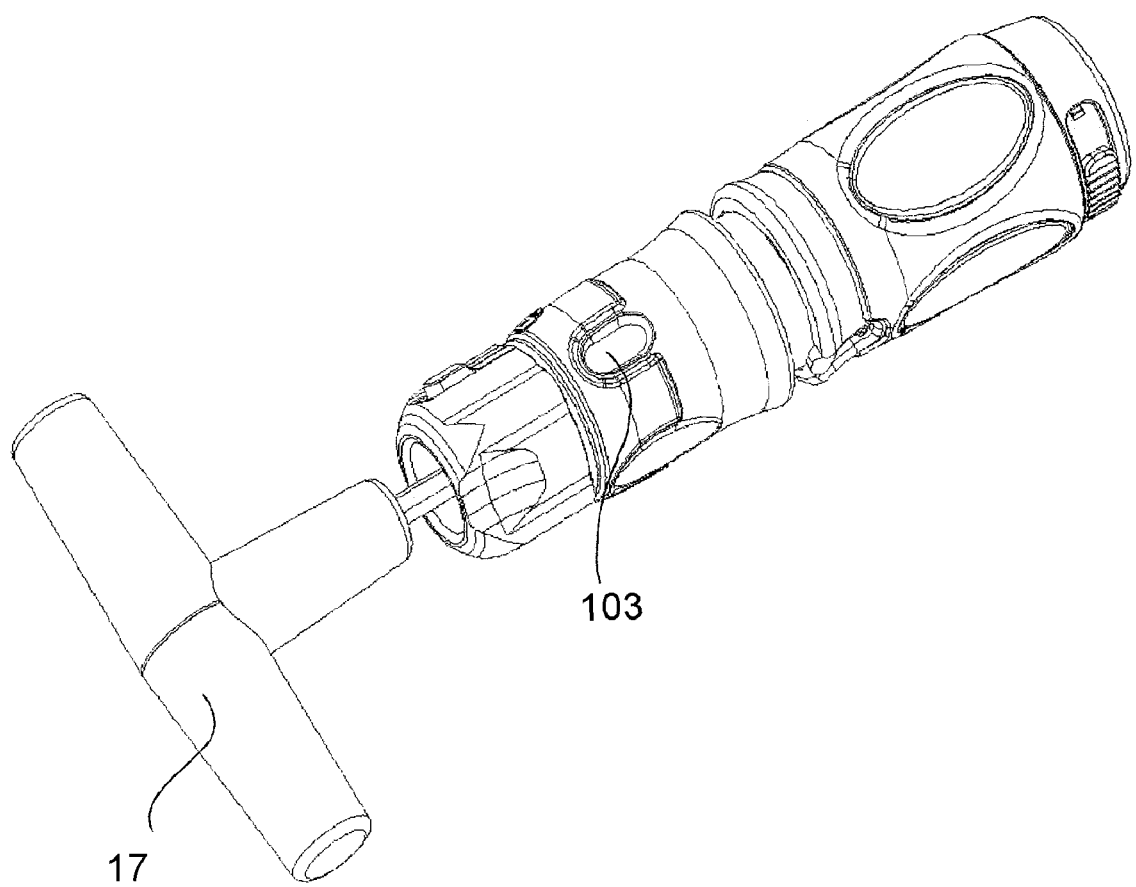
FIG. 25 is a perspective view of an injection device with pressure-adjustment key inserted therein.
Figure 26:
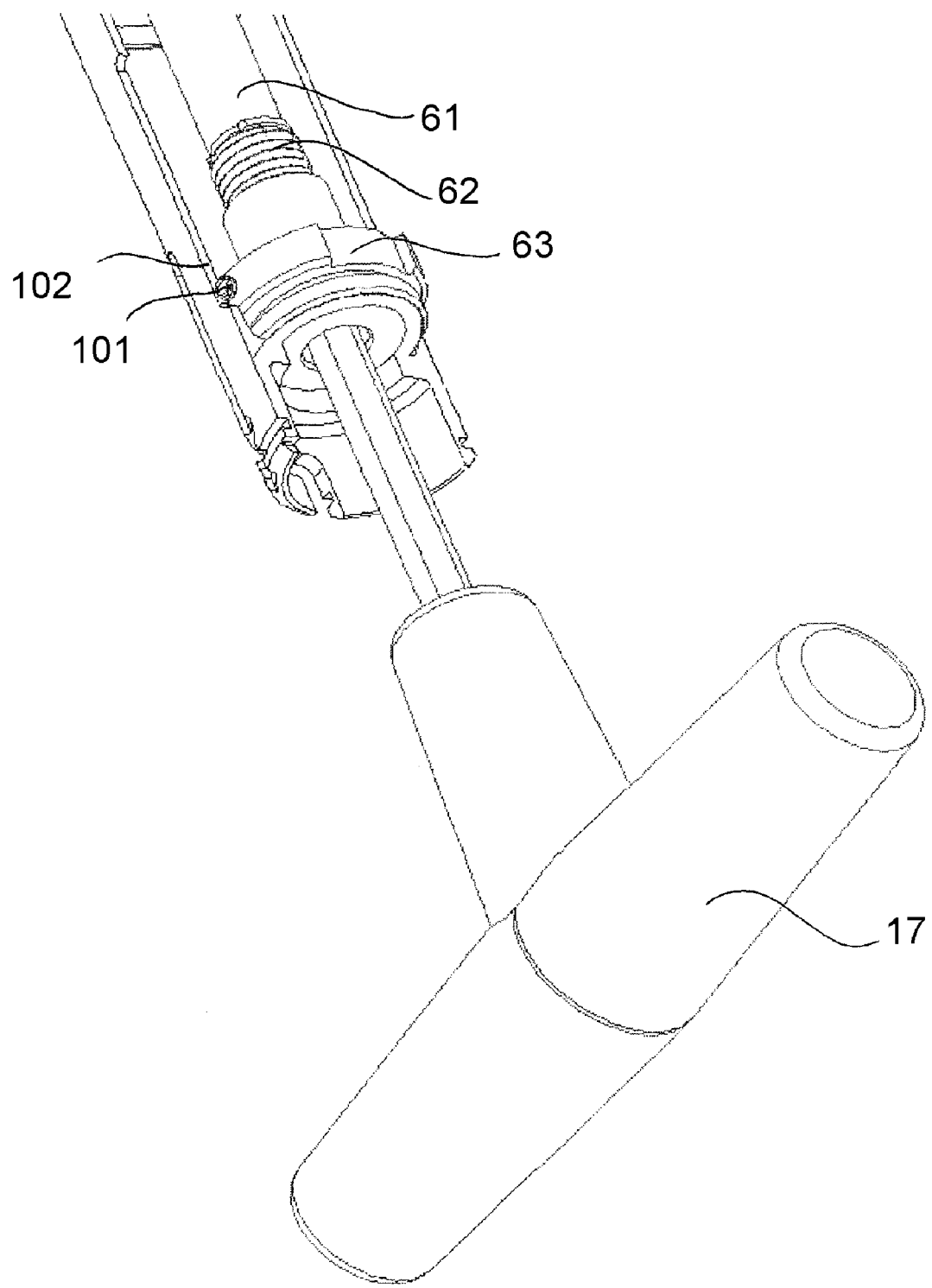
FIG. 26 is a cut-away view of part of the injection device, showing the pressure adjustment facility.

With reference to FIGS. 25 and 26, a key 17 is provided which fits into the front end of the injection device (the nozzle assembly having being removed as described above).

With the nozzle assembly removed from the device, the key 17 can be inserted through the front end of the device to engage with the front end of the ram 61 (through the nut 63). The internally screw-threaded nut 63 is rotationally-fixed with respect to the housing by means of a pin 101 confined within a slot 102.

The key can be turned which causes the whole ram 61 to rotate with respect to the housing. During this rotation of the ram 61, the screw-threaded portion 62 at the front end of the ram co-operates with the screw-thread on nut 63 to reduce or enlarge the volume of the chamber in which the main spring 77 is confined (depending upon the direction in which the ram is rotated). By varying the volume of the chamber in which the main spring is confined, the maximum compressive firing force which can be stored in the spring is also varied. This provides a safe and easy way of adjusting the firing force without the need to disassemble the injection device. The key can be kept by an adult or carer to avoid inadvertent use by a young patient.

Optionally, a window 103 is provided in the housing to allow visual feedback of the pressure adjustment (see FIG. 25).

Figure 28:
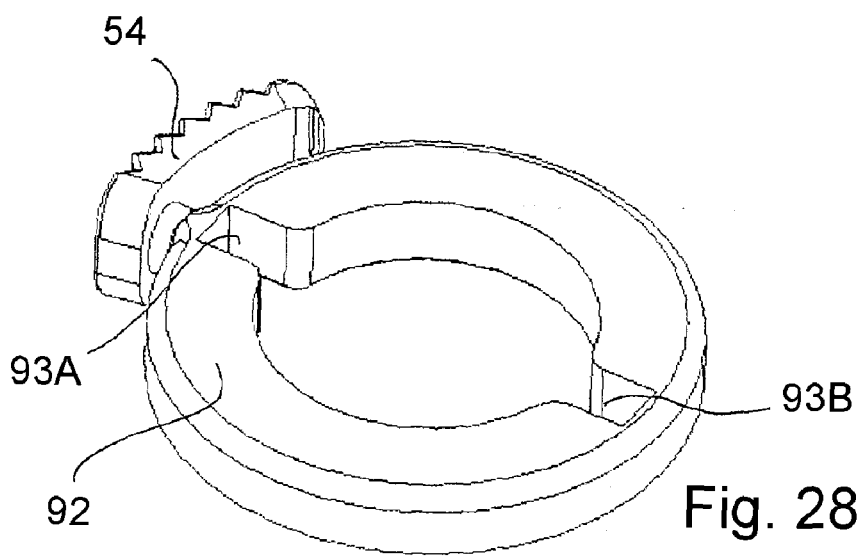
FIG. 28 shows the drive plate including the sliding switch.
Figure 29:
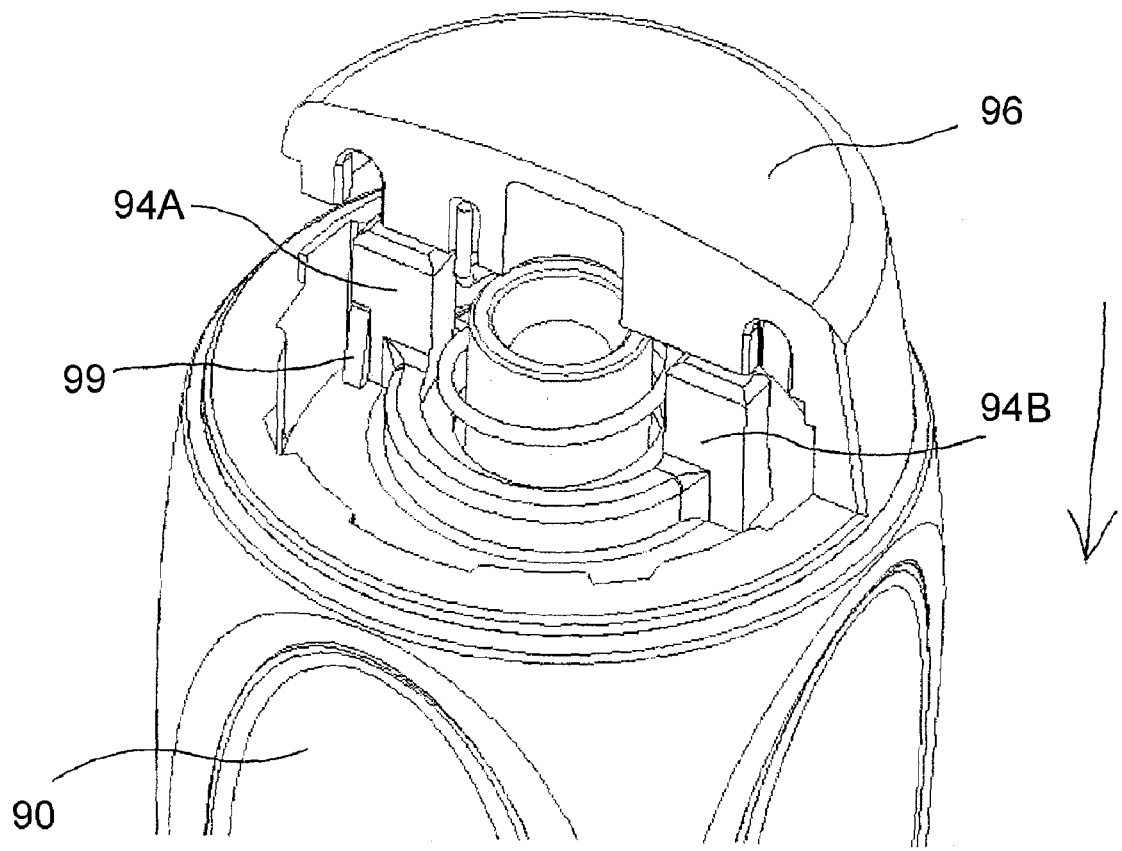
FIG. 29 shows, in greater detail, the operation of the safety lock mechanism with optional clip.

An optional modification to the safety lock mechanism will now be described with reference to FIGS. 27-29.

In the embodiment described above, until the sliding switch is slid into the correct position, the device cannot be fired because the tabs 94A, 94B abut the endcap 96. The switch 54 is biased into the "safe" position from which the device cannot be fired and therefore the user must slide the switch 54 to the "firing" position and then hold it there whilst simultaneously applying axial pressure to the shroud in order to fire the device.

Figure 27:
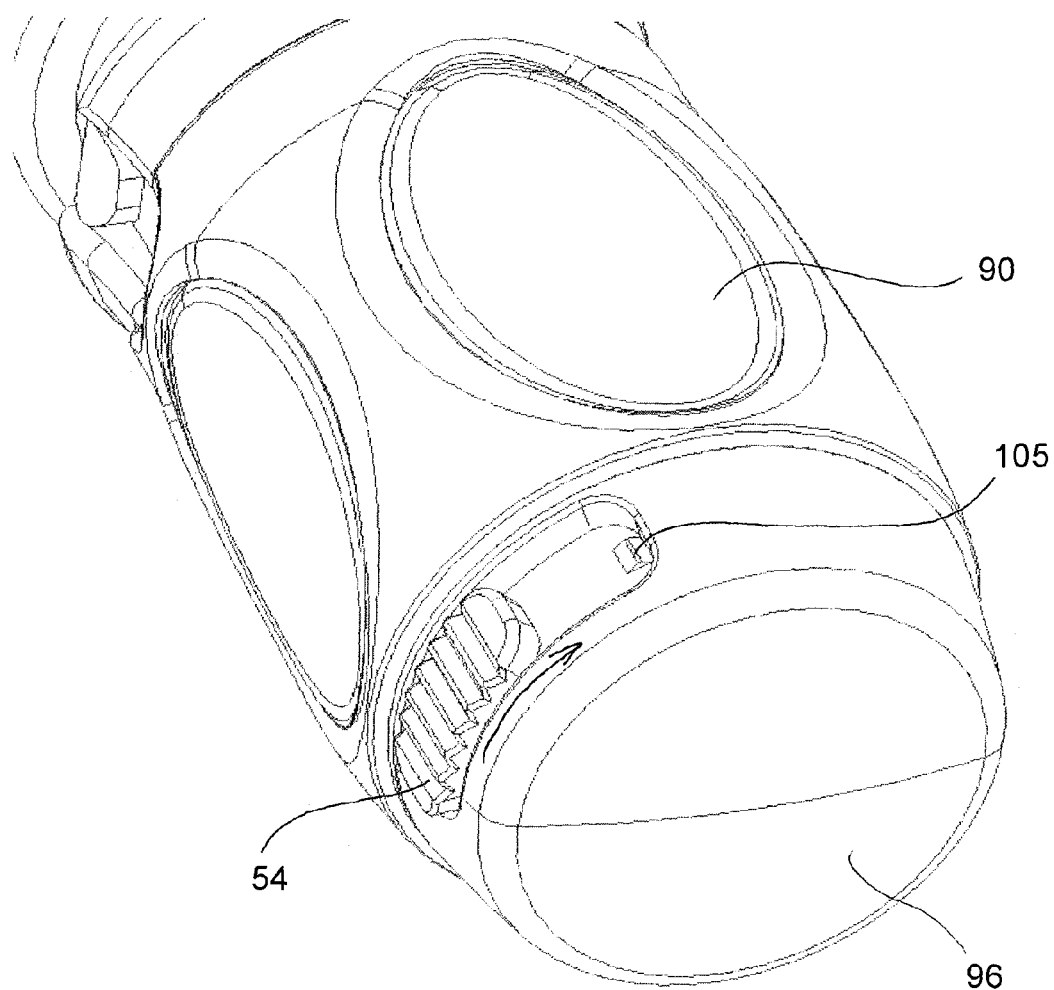
FIG. 27 shows the optional clip in the safety lock mechanism.

In the embodiment illustrated in FIG. 27, an intermediate position is available in which the device is ready to fire (i.e. safety lock is released) but does not require the user to hold the sliding switch 54 in the "firing" position (in other words the bias into the "safe" position is temporarily overridden).

Referring to FIG. 27, the sliding switch 54 is illustrated in the "safe" position from which the device cannot be fired. There is provided a clip 105 onto which the sliding switch 54 can be hooked when the sliding switch is slid into the "firing" position in the direction indicated by the arrow in FIG. 27. When the sliding switch 54 is hooked onto the clip 105, the device is able to be fired, and the sliding switch 54 does not slide back into the "safe" position.

Therefore the user is free to apply axial pressure to the shroud 90 in the usual way in order to fire the device. When such axial pressure is applied to the shroud as indicated by the arrow in FIG. 29, the endcap 96 transmits downward force to the tabs 94A, 94B thus firing the device as described above. Wedges 99, formed on the tabs, cooperate with corresponding surfaces of the drive plate 92 so that the downward axial (linear) motion of the tabs causes a slight rotary motion of the drive plate 92, sufficient to knock the sliding switch 54 off the clip 105. Once free of the clip 105, the sliding switch 54 is biased back into the "safe" position, ready for the next use of the device.

The invention claimed is:

1. A needleless injection device, comprising:
a cylinder for medicament having an injection nozzle at a forward end thereof and an opening at its rearward end;
a piston sliding in the cylinder through said open end, in use, to drive the medicament through the nozzle;
a ram to drive the piston into the cylinder and having a longitudinal axis; and
an energy accumulator to drive the ram when discharged and disposed between the ram and a discharge assembly, a rear end of the ram extending into said discharge assembly;
wherein the discharge assembly comprises a retention member fixed in the assembly, said retention member having a plurality of retention elements spaced around and adapted to locate on the ram when in a charged position of the ram, and a release ring surrounding said retention elements to prevent radial outward displacement thereof and discharge of the ram;
wherein axial displacement of said release ring releases said retention elements and causes discharge of the ram by said accumulator;
wherein said retention elements are integral with said retention member and each has an enlarged head which can move into and out of engagement with a groove or recess on the ram by deformation of the material of said retention member; and
wherein said retention member comprises a collet having radially spreadable fingers that are flexible and bias radially-inwardly, and wherein said collet in use moves between said first position in which said fingers engage with said ram and said second position in which said fingers spread radially out of engagement with said ram.

2. A device as claimed in claim 1, wherein said release ring comprises a collet lock sleeve which limits outward radial movement of said collet fingers.

3. A device as claimed in claim 2, wherein axial movement of said collet lock sleeve is limited by abutment thereof against said collet fingers.

4. A device as claimed in claim 3, wherein said collet lock sleeve and said collet fingers are respectively provided with cooperating tapered surfaces.

5. A device as claimed in claim 2, wherein said collet lock sleeve and said collet fingers are respectively provided with cooperating tapered surfaces.

6. A device as claimed in claim 1, wherein said release ring comprises a collet lock sleeve which limits outward radial movement of said collet fingers.

7. A device as claimed in claim 6 wherein axial movement of said collet lock sleeve is limited by abutment thereof against said collet fingers.

8. A device as claimed in claim 1, wherein said energy accumulator is a compression spring.

9. A device as claimed in claim 1, further comprising a nozzle lock assembly which enables a nozzle to be releasably attached to said device upon insertion of a nozzle into an end thereof, the nozzle lock assembly comprising:
on one of said nozzle or said end of the injection device, a twist cap containing a moveable spacer which has a non-circular aperture therethrough; and
on the other of said nozzle or said end of the injection device a protrusion having a correspondingly shaped non-circular outer surface which, if aligned therewith, can pass through said non-circular aperture,
wherein, upon twisting of said twist cap, the moveable spacer twists with respect to said protrusion so that the non-circular aperture of the spacer can be selectively brought into and out of alignment with the non-circular outer surface of said protrusion, so that said protrusion is respectively either free to move in or out of said aperture or is trapped therein by said moveable spacer.

10. A device as claimed in claim 9, wherein said twist cap is located on said end of the injection device and said protrusion is located on said nozzle.

11. A device as claimed in claim 10, further comprising a second protrusion having the same non-circular outer surface and being axially spaced from the first protrusion.

12. A device claimed in claim 9, further comprising a second protrusion having the same non-circular outer surface and being axially spaced from the first protrusion.

13. A device as claimed in claim 9, wherein said non-circular aperture and said non-circular outer surface are substantially triangular.

14. A device as claimed in claim 9, further comprising a mark on said twist cap which indicates the relative alignment of the non-circular aperture and the protrusion.

15. A device as claimed in claim 1, wherein said axial displacement comprises a resistance-sensitive trigger comprising an axially-moveable shroud forming at least part of the outer surface of said device, the trigger being activated by application of forward axial force to the shroud which is resisted by the skin of the patient at an injection site.

16. A device as claimed in claim 15, wherein said resistance-sensitive trigger further comprises a safety-lock, moveable between a locked position, in which the device cannot be discharged and an unlocked position in which the device can be discharged.

17. A device as claimed in claim 16, wherein said safety lock comprises at least one axially-extending tab which serves as an endstop which, in said locked position, prevents axial movement of said shroud.

18. A device as claimed in claim 17, wherein said tab is driveable between said unlocked positions by a rotatable drive plate actuated by a switch.

19. A device as claimed in claim 17, wherein, in said unlocked position, said tab moves axially rearward to engage in a recess in an endcap of the injection device.

20. A device as claimed in claim 19, wherein said tab is rearwardly biassed by means of a spring.

21. A device as claimed in claim 1, wherein said energy accumulator is a spring confined within a variable-volume chamber, the injection device further comprising an integral firing force adjustment mechanism which, in use, varies the volume of said chamber, effected by rotation of said ram.

22. A device as claimed in claim 21, wherein the rotation of the ram is effected by the turning of a key inserted through one end of said device.

* * * * *